(12) United States Patent
Sagi et al.

(10) Patent No.: US 8,324,355 B2
(45) Date of Patent: Dec. 4, 2012

(54) ANTIBODIES AND PHARMACEUTICAL COMPOSITIONS CONTAINING SAME USEFUL FOR INHIBITING ACTIVITY OF METALLOPROTEINS

(75) Inventors: Irit Sagi, Rechovot (IL); Tamar Danon, Kfar Uriah-Doar-Na Shimshon (IL); Netta Sela, Doar-Na Emek Hefer (IL); Abraham Shanzer, Rechovot (IL); Rina Arad-Yellin, Rechovot (IL); Raghavendra Kikkeri, Mysore (IN)

(73) Assignee: Yeda Reearch and Development Co. Ltd, Rehovot (IL)

( * ) Notice: Subject to any disclaimer, the term of this patent is extended or adjusted under 35 U.S.C. 154(b) by 417 days.

(21) Appl. No.: 12/449,728

(22) PCT Filed: Feb. 21, 2008

(86) PCT No.: PCT/IL2008/000230
§ 371 (c)(1),
(2), (4) Date: Aug. 24, 2009

(87) PCT Pub. No.: WO2008/102359
PCT Pub. Date: Aug. 28, 2008

(65) Prior Publication Data
US 2010/0233188 A1    Sep. 16, 2010

Related U.S. Application Data

(60) Provisional application No. 60/902,854, filed on Feb. 23, 2007.

(51) Int. Cl.
  *C07K 16/00* (2006.01)
(52) U.S. Cl. ............... 530/389.8; 530/388.9; 424/175.1
(58) Field of Classification Search .................. None
  See application file for complete search history.

(56) References Cited

U.S. PATENT DOCUMENTS

| | | | |
|---|---|---|---|
| 4,595,700 A | 6/1986 | Donald et al. | |
| 6,492,422 B2 | 12/2002 | O'Brien et al. | |
| 6,495,699 B2 | 12/2002 | Bender et al. | |
| 7,524,938 B2 * | 4/2009 | Sagi et al. | 530/388.26 |

FOREIGN PATENT DOCUMENTS

| | | |
|---|---|---|
| EP | 0757984 | 2/1997 |
| EP | 0780386 | 6/1997 |
| WO | WO 90/05719 | 5/1990 |
| WO | WO 93/20047 | 10/1993 |
| WO | WO 95/09841 | 4/1995 |
| WO | WO 95/29689 | 11/1995 |
| WO | WO 95/29892 | 11/1995 |
| WO | WO 96/06074 | 2/1996 |
| WO | WO 97/24117 | 7/1997 |
| WO | WO 97/49679 | 12/1997 |
| WO | WO 2004/087042 | 10/2004 |
| WO | WO 2008/102359 | 1/2008 |

OTHER PUBLICATIONS

Examination Report Dated Nov. 23, 2011 From the ROSPATENT, Federal Government Institution, Federal Institute of Industrial Property of the Federal Service for Intellectual Property, Patents and Trademarks of the Russian Federation Re. Application No. 2009132006 and its Summary in English.
Massova et al. "Matrix Metalloproteinases: Structures, Evolution, and Diversification", The FASEB Journal, 12: 1075-1095, 1998.
Axisa et al. "Prospective, Randomized, Double-Blind Trial Investigating the Effect of Doxycycline on Matrix Metalloproteinase Expression Within Atherosclerotic Carotid Plaques", Stroke, 33: 2858-2865, 2002.

(Continued)

*Primary Examiner* — Shafiqul Haq

(57) ABSTRACT

The present invention relates to a compound having the general Formula (I):

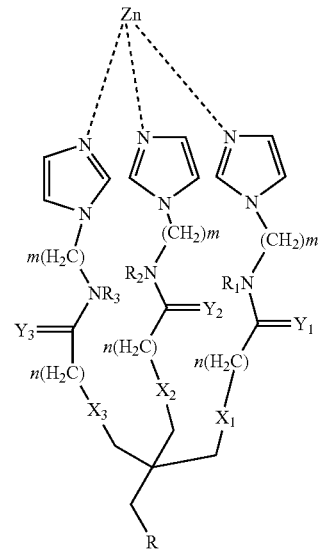

wherein:
m and n are each independently an integer from 1 to 6;
$X_1$-$X_3$ and $Y_1$-$Y_3$ are each independently O or S;
$R_1$-$R_3$ are each independently selected from the group consisting of hydrogen, alkyl, and cycloalkyl; and
R is $(CH_2)x$-$C(=O)NR'$—$(CH_2)y$-$NR'R''$
whereas:
x and y are each independently an integer from 1 to 6; and
R' and R" are each independently selected from the group consisting of hydrogen, alkyl, and cycloalkyl; and to an antibody comprising an antigen recognition region capable of specifically binding the above compound.

3 Claims, 16 Drawing Sheets
(10 of 16 Drawing Sheet(s) Filed in Color)

OTHER PUBLICATIONS

Bode et al. "The X-Ray Crystal Structure of the Catalytic Domain of Human Neutrophil Collagenase Inhibited by A Substrate analogue Reveals the Essentials for Catalysis and Specificity", The EMBO Journal, 13(6): 1263-1269, 1994.

Dean et al. "Evidence for Metalloproteinase and Metalloproteinase Inhibitor Imbalance in Human Osteoarthritic Cartilage", Journal of Clinical Investigation, 84: 678-685, Aug. 1989.

Denis et al. "Matrix Metalloproteinase Inhibitors: Present Achievements and Future Prospects", Investigational New Drugs, 15: 175-185, 1997.

Gálvez et al. "Membrane Type 1-Matrix Metalloproteinase is Activated During Migration of Human Endothelial Cells and Modulates Endothelial Motility and Matrix Remodeling", The Journal of Biological Chemistry, 276(40): 37491-37500, Oct. 5, 2001.

Grams et al. "Structure Determination and Analysis of Human Neutrophil Collagenase Complexed With A Hydroxamate Inhibitor", Biochemistry, 34: 14012-14020, 1995.

Heath et al. "Phase I Trial of the Matrix Metalloproteinase Inhibitor BAY12-9566 in Patients With Advanced Solid Tumors", Cancer Chemotherapy and Pharmacology, 48: 269-274, 2001.

Hill et al. "Inhibition of Bone Resorption in Vitro by Selective Inhibitors of Gelatinase and Collagenase", Biochemical Journal, 308: 167-175, 1995.

Hodgson "Remodeling MMPIs. Matrix Metalloproteinase Inhibitors Will Be Approved as Drugs, Probably This Year, But Questions Remain Concerning Their Specificity, Bioavailability, and Potential Long-Term Toxicity", Bio/Technology, 13: 554-557, Jun. 1995.

Kleifeld et al. "X-Ray Absorption Studies of Human Matrix Metalloproteinase-2 (MMP-2) Bound to A Highly Selective Mechanism-Based Inhibitor", The Journal of Biological Chemistry, 276(20): 17125-17131, May 18, 2001.

Levitt et al. "Phase I and Pharmacological Study of the Oral Matrix Metalloproteinase Inhibitor, MM1270 (CGS27023A), in Patients With Advanced Solid Cancer", Clinical Cancer Research, 7: 1912-1922, Jul. 2001.

Ochieng et al. "Galectin-3 is A Novel Substrate for Human Matrix Metalloproteinases-2 and -9", Biochemistry, 33: 14109-14114, 1994.

Patterson et al. "Angiostatin-Converting Enzyme Activities of Human Matrilysin (MMP-7) and Gelatinase B/Type IV Collagenase (MMP-9)", the Journal of Biological Chemistry, 272(46): 28823-28825, Nov. 14, 1997.

Rasmussen et al. "Matrix Metalloproteinase Inhibition as A Novel Anticancer Strategy: A Review With Special Focus on Batmastat and Marimastat", Phamacology and Therapy, 75(1): 69-75, 1997.

Schwartz et al. "8 Synthetic Inhibitors of Bacterial and Mammalian Interstitial Collagenases", Progress in Medicinal Chemistry, 29: 271-334, 1992.

Sheu et al. "A Novel Role of Metalloproteinase in Cancer-Mediated Immunosuppression", Cancer Research, 61: 237-242, Jan. 1, 2001.

Singh et al. "Relationship Between Structure and Bioavailability in A Series of Hydroxamate Based Metalloprotease Inhibitors", Bioorganic & Medicinal Chemistry Letters, 5(4): 337-342, 1995.

Van den Steen et al. "Neutrophil Gelatinase B Potentiates Interleukin-8 Tenfold by Aminoterminal Processing, Whereas It Degrades CTAP-III, PF-4, and GRO-Alpha and Leaves RANTES and MCP-2 Intact", Blood, 96: 2673-2681, 2000.

Walakovits et al. "Detection of Stromelysin and Collagenase in Synovial Fluid From Patients With Rheumatoid Arthritis and Post-traumatic Knee Injury", Arthritis and Rheumatism, 35(1): 35-42, Jan. 1992.

Yu et al. "Cell Surface-Localized Matrix Metalloproteinase-9 Proteolytically Activates TGF-$\beta$ and Promotes Tumor Invasion and Angiogenesis", Genes & Development, 14: 163-176, 2000.

Zucker et al. "Critical Appraisal of the Use of matrix Metalloproteinase Inhibitors in Cancer Treatment", Oncogene, 19: 6642-6650, 2000.

International Search Report and the Written Opinion Dated Jul. 23, 2008 From the International Searching Authority Re.: Application No. PCT/IL2008/000230.

Translation of Office Action Dated May 6, 2011 From the State Intellectual Property Office of the People's Republic of China Re. Application No. 200880012673.1.

* cited by examiner

[meso-Tetrakis (4-carboxyphenyl)-porphyrinato] zinc (II)

[meso-Tetrakis (4-carboxyphenyl)-porphyrinato] cobalt (II)

tris-[2-(N-(3-imidazol-1-yl-propyl) -[2-(2-aminoethylcarbomoyl) -ethoxymethyl] -ethoxymethyl]methane MMP-9 zinc binding motif ZnTCPP(15E12)

CoTCPP(13E11)

Imisdp(6C6)

MMP-9

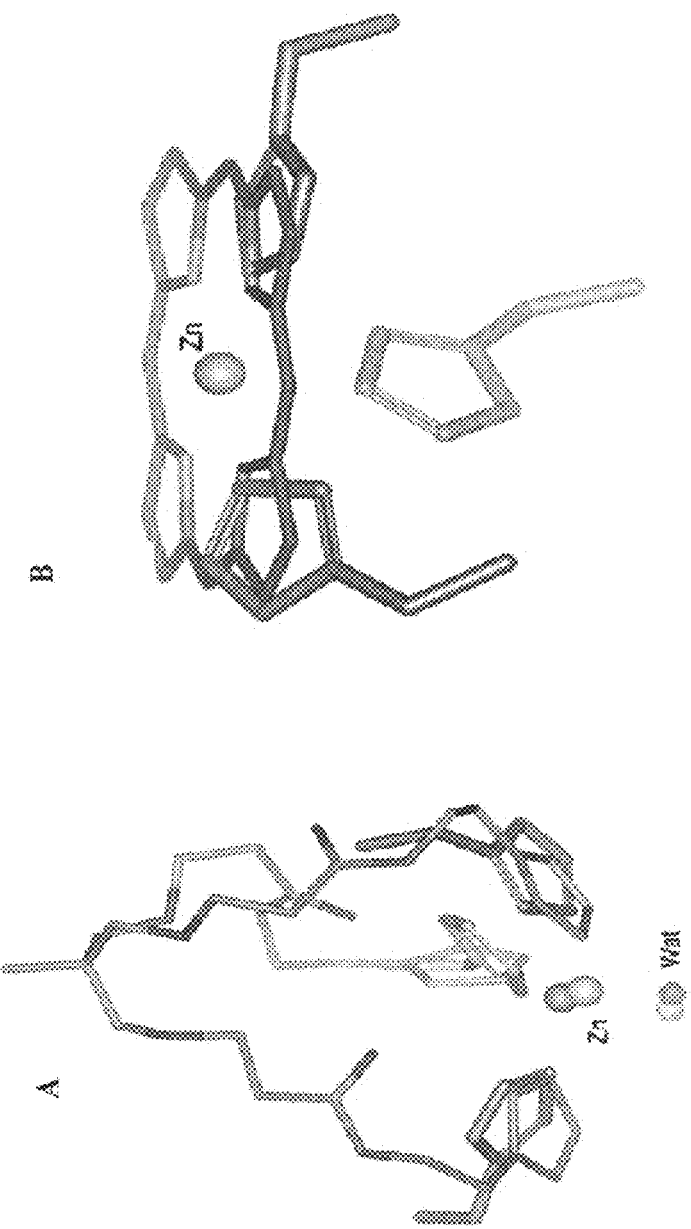
Figs. 2A-B

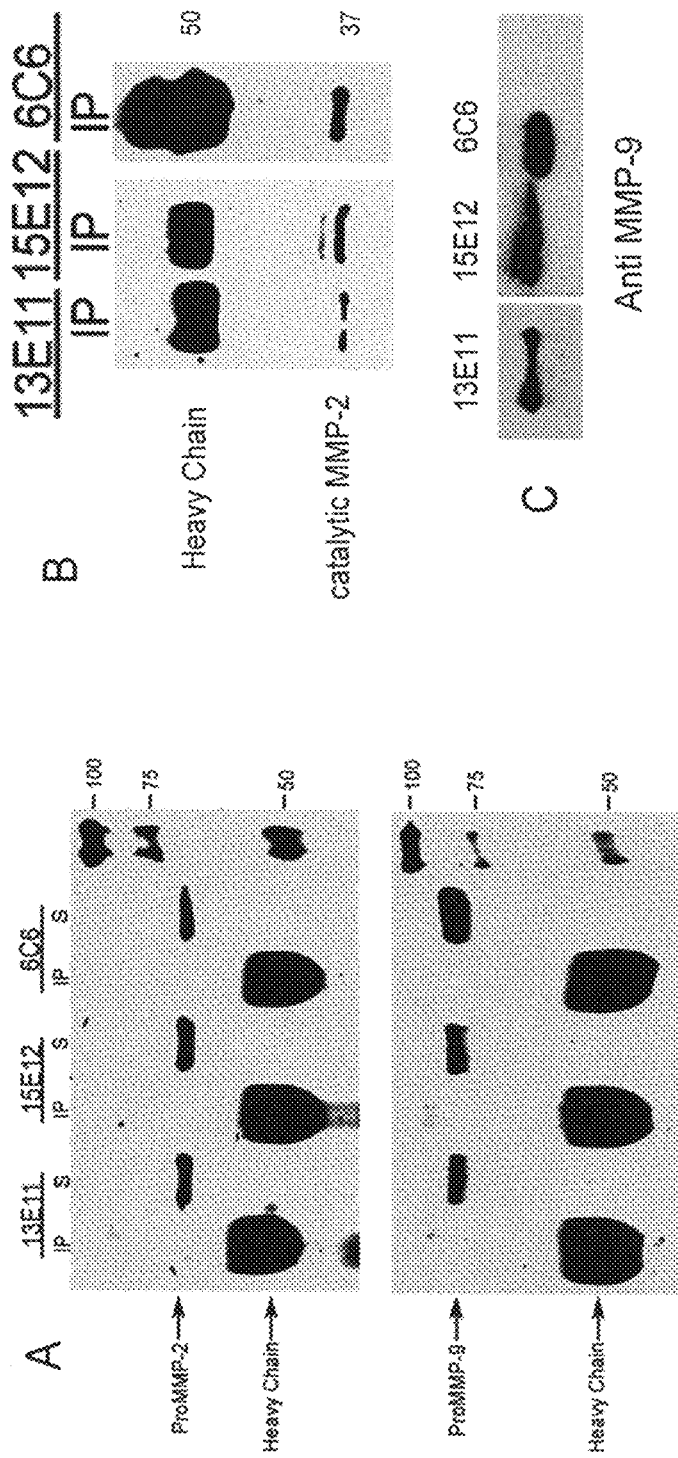
Figs. 3A-C

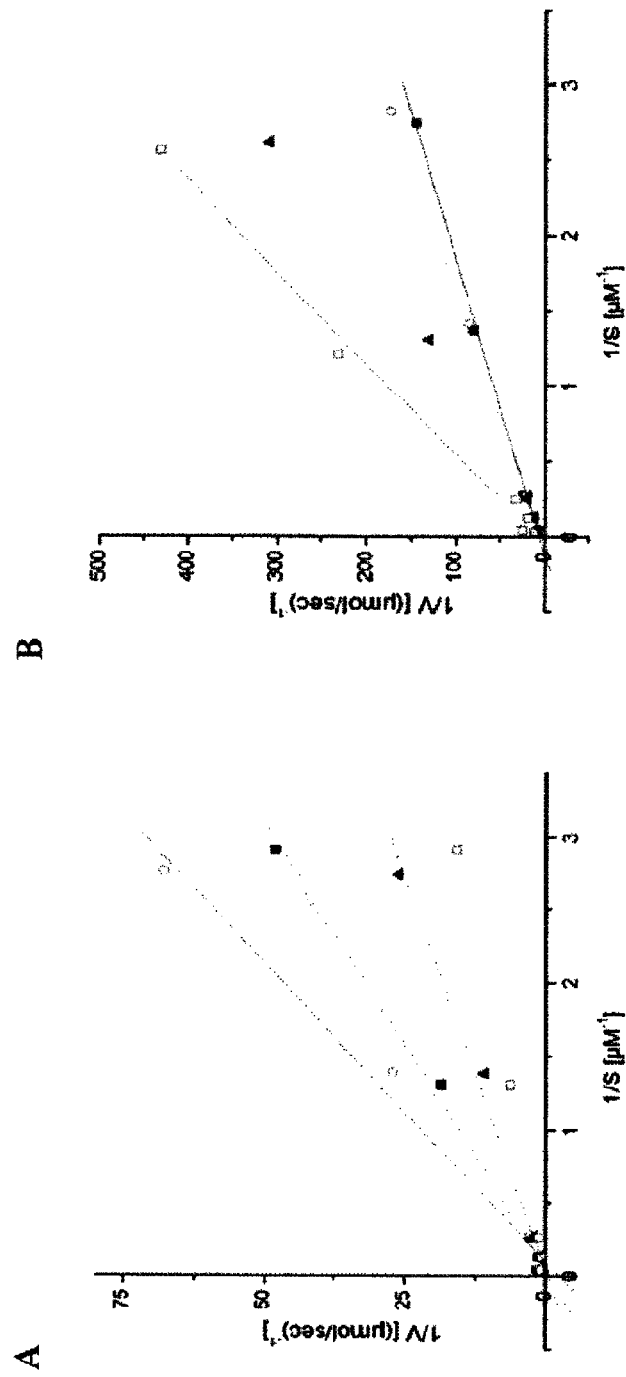
Figs. 4A-B

Fig. 10 CDR sequences of mAbs 13E11, 15E12 and 6C6 aligned

```
13E11 CoTCPP  RASSSVS------YMHW      YATSNLAS   QQWISNPLT
15E12 ZnTCPP  RSSQSIVQSNGNTYLDW      YKVSNRFS   FQGSHVPYT
6C6   Imisdp  RSSQSIVHSNGNTFLEW      YKVSNRFS   FQASHVPPT 13E11 CoTCPP  SFGMH    YISSG-NIIYYADTVKGR    RNYYRYGFYVMD
15E12 ZnTCPP  SYDIS    VMWSG-GGTNYNSAFMSR    GRLHYYGYWFFD
6C6   Imisdp  TYDMS    TISSGGSYTYPDSVKGR     R---FRYDGWYFD
```

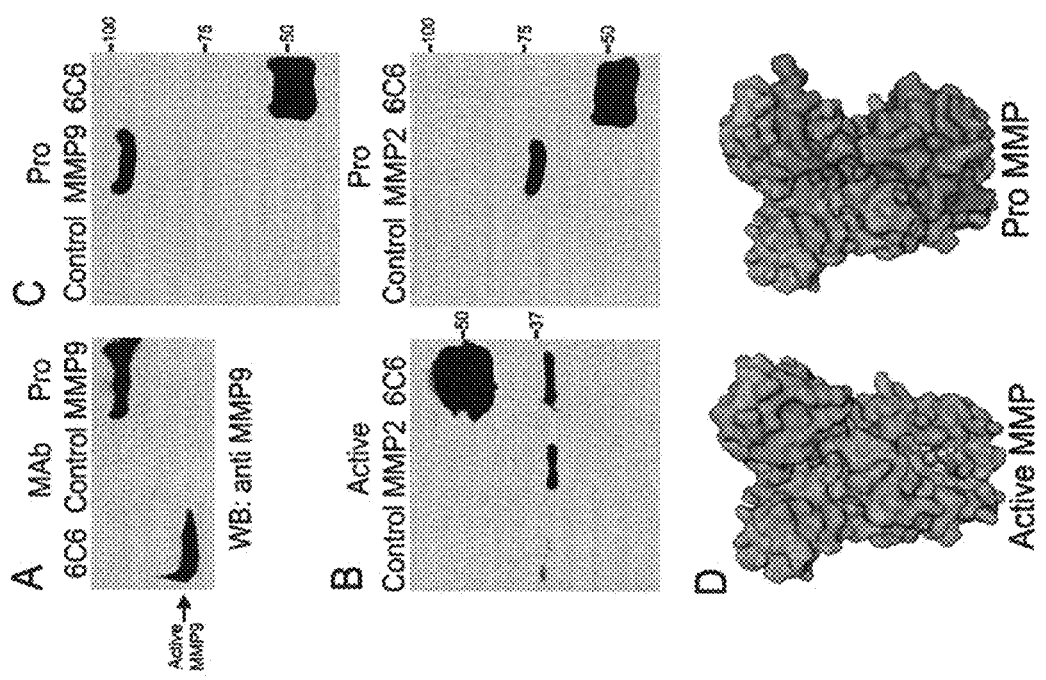
FIGs. 11A-D

FIGs. 12A-B
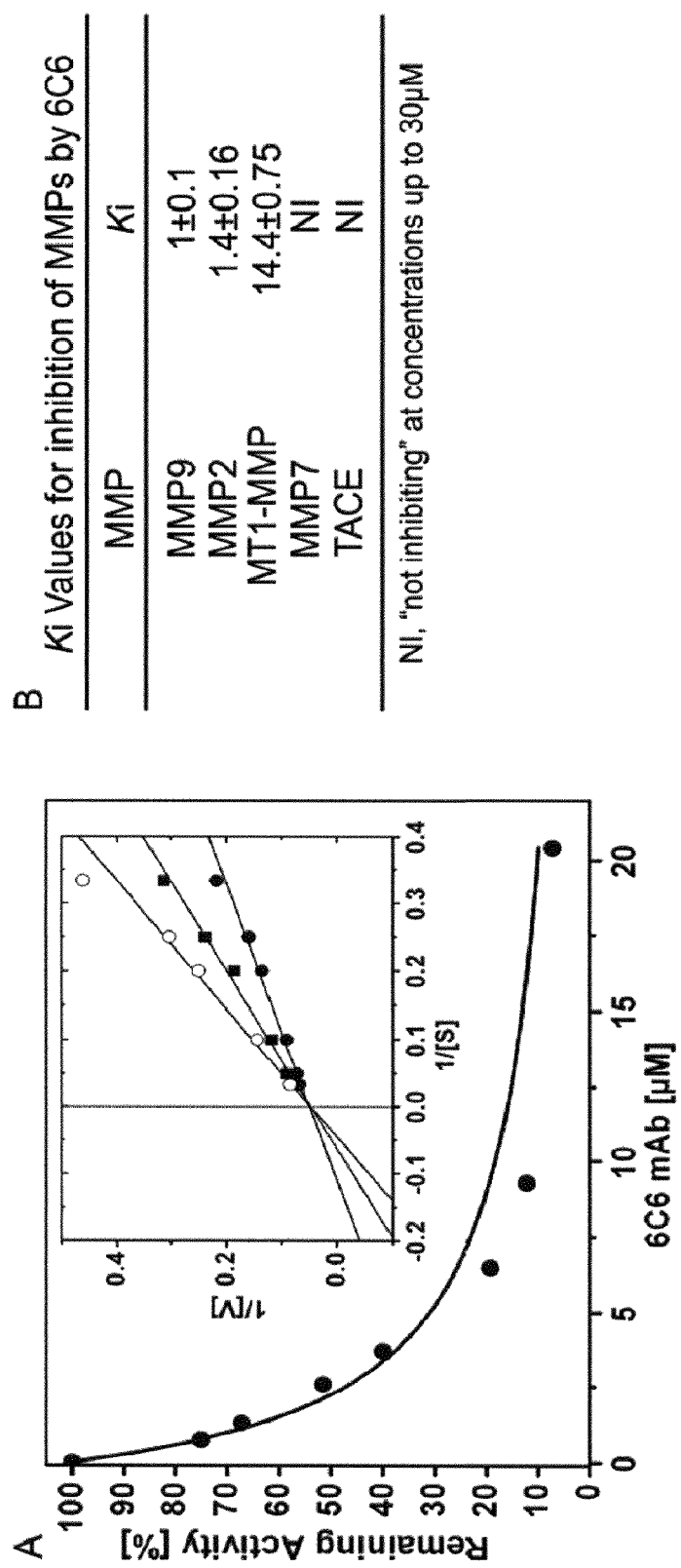

FIGs. 14A-C

FIGs. 15A-C

SEQUENCE LISTING

```
<160> NUMBER OF SEQ ID NOS: 18

<210> SEQ ID NO 1
<211> LENGTH: 107
<212> TYPE: PRT
<213> ORGANISM: Artificial sequence
<220> FEATURE:
```

<223> OTHER INFORMATION: 6c6 mAb light chain

<400> SEQUENCE: 1

Cys Met Glu Thr Thr Gln Thr Pro Leu Ser Leu Pro Val Ser Leu Gly
1               5                   10                  15

Asp Gln Ala Ser Ile Ser Cys Arg Ser Ser Gln Ser Ile Val His Ser
            20                  25                  30

Asn Gly Asn Thr Phe Leu Glu Trp Tyr Leu Gln Lys Pro Gly Gln Ser
        35                  40                  45

Pro Lys Leu Leu Ile Tyr Lys Val Ser Asn Cys Arg Phe Ser Gly Val
    50                  55                  60

Pro Asp Arg Phe Ser Gly Ser Gly Ser Gly Thr Asp Phe Thr Leu Lys
65                  70                  75                  80

Ile Ser Arg Val Glu Ala Glu Asp Leu Gly Val Tyr Tyr Cys Phe Gln
                85                  90                  95

Ala Ser His Val Pro Pro Thr Phe Gly Gly Gly
            100                 105

<210> SEQ ID NO 2
<211> LENGTH: 107
<212> TYPE: PRT
<213> ORGANISM: Artificial sequence
<220> FEATURE:
<223> OTHER INFORMATION: 15E12 mAb light chain

<400> SEQUENCE: 2

Glu Met Glu Thr Thr Gln Thr Pro Leu Ser Leu Pro Val Ser Leu Gly
1               5                   10                  15

Asp Gln Ala Ser Ile Ser Cys Arg Ser Ser Gln Ser Ile Val Gln Ser
            20                  25                  30

Asn Gly Asn Thr Tyr Leu Asp Trp Tyr Leu Gln Lys Pro Gly Gln Ser
        35                  40                  45

Pro Lys Leu Leu Ile Tyr Lys Val Ser Asn Glu Arg Phe Ser Gly Val
    50                  55                  60

Pro Asp Arg Phe Ser Gly Ser Gly Ser Gly Thr Asp Phe Thr Leu Lys
65                  70                  75                  80

Ile Ser Arg Val Glu Ala Asp Asp Leu Gly Val Tyr Tyr Cys Phe Gln
                85                  90                  95

Gly Ser His Val Pro Tyr Thr Phe Gly Gly Gly
            100                 105

<210> SEQ ID NO 3
<211> LENGTH: 101
<212> TYPE: PRT
<213> ORGANISM: Artificial sequence
<220> FEATURE:
<223> OTHER INFORMATION: 13E11 mAb light chain

<400> SEQUENCE: 3

Glu Ile Val Val Thr Gln Ser Pro Ala Ile Leu Ser Ala Ser Pro Gly
1               5                   10                  15

Glu Lys Val Thr Met Thr Cys Arg Ala Ser Ser Ser Val Ser Tyr Met
            20                  25                  30

His Trp Tyr Gln Gln Lys Pro Gly Ser Ser Pro Lys Pro Trp Ile Tyr
        35                  40                  45

Ala Thr Ser Asn Glu Leu Ala Ser Gly Val Pro Ala Arg Phe Ser Gly
    50                  55                  60

Ser Gly Ser Gly Thr Ser Tyr Ser Leu Thr Ile Ser Arg Val Glu Ala
65                  70                  75                  80

```
Glu Asp Ala Ala Thr Tyr Tyr Cys Gln Gln Trp Ile Ser Asn Pro Leu
                85                  90                  95

Thr Phe Gly Ala Gly
            100

<210> SEQ ID NO 4
<211> LENGTH: 108
<212> TYPE: PRT
<213> ORGANISM: Artificial sequence
<220> FEATURE:
<223> OTHER INFORMATION: 13E11 mAb heavy chain

<400> SEQUENCE: 4

Glu Gly Gly Gly Leu Val Gln Pro Gly Gly Ser Arg Lys Leu Ser Cys
1               5                   10                  15

Ala Ala Ser Gly Phe Thr Phe Thr Ser Phe Gly Met His Trp Val Arg
                20                  25                  30

Gln Ala Pro Glu Lys Gly Leu Glu Trp Val Ala Tyr Ile Ser Ser Gly
            35                  40                  45

Asn Glu Ile Ile Tyr Tyr Ala Asp Thr Val Lys Gly Arg Phe Thr Ile
50                  55                  60

Ser Arg Asp Asn Pro Lys Asn Thr Leu Phe Leu Gln Met Thr Ser Leu
65                  70                  75                  80

Arg Ser Glu Asp Thr Ala Met Tyr Tyr Cys Ala Arg Asn Tyr Tyr Arg
                85                  90                  95

Tyr Gly Phe Tyr Val Met Asp Tyr Trp Gly Gln Gly
            100                 105

<210> SEQ ID NO 5
<211> LENGTH: 114
<212> TYPE: PRT
<213> ORGANISM: Artificial sequence
<220> FEATURE:
<223> OTHER INFORMATION: 15E12 mAb heavy chain

<400> SEQUENCE: 5

Glu Gly Pro Gly Leu Val Ala Pro Ser Gln Ser Leu Ser Ile Thr Cys
1               5                   10                  15

Thr Val Ser Gly Ile Ser Leu Ser Ser Tyr Asp Ile Ser Trp Ile Arg
                20                  25                  30

Gln Pro Pro Gly Lys Gly Leu Glu Trp Leu Gly Val Met Glu Thr Trp
            35                  40                  45

Ser Gly Gly Gly Thr Glu Asn Tyr Asn Ser Ala Phe Met Glu Thr Ser
    50                  55                  60

Arg Leu Ser Ile Ser Lys Asp Asn Ser Lys Arg Gln Val Phe Leu Asn
65                  70                  75                  80

Met Glu Thr Asn Ser Val Gln Ile Asp Asp Thr Ala Thr Tyr Tyr Cys
                85                  90                  95

Ile Gly Arg Leu His Tyr Tyr Gly Tyr Trp Phe Leu Asp Val Trp Asp
            100                 105                 110

Gln Gly

<210> SEQ ID NO 6
<211> LENGTH: 111
<212> TYPE: PRT
<213> ORGANISM: Artificial sequence
<220> FEATURE:
<223> OTHER INFORMATION: 6c6 mAb heavy chain

<400> SEQUENCE: 6
```

-continued

Cys Gly Gly Leu Val Lys Pro Gly Ser Leu Lys Leu Ser Cys
1               5                   10                  15

Ala Ala Ser Gly Phe Ala Phe Ser Thr Tyr Asp Met Glu Thr Ser Trp
            20              25                  30

Ile Arg Gln Thr Pro Glu Lys Arg Leu Glu Trp Val Ala Thr Ile Ser
            35              40                  45

Ser Gly Gly Ser Cys Tyr Thr Tyr Tyr Pro Asp Ser Val Lys Gly Arg
        50              55                  60

Phe Thr Ile Ser Lys Asp Asn Ala Arg Asn Thr Leu Tyr Leu Gln Met
65              70                  75                  80

Glu Thr Ser Ser Leu Arg Ser Gly Asp Thr Ala Leu Tyr Tyr Cys Thr
                85                  90                  95

Arg Phe Arg Tyr Asp Gly Trp Tyr Phe Asp Val Trp Gly Gln Gly
            100                 105                 110

<210> SEQ ID NO 7
<211> LENGTH: 17
<212> TYPE: PRT
<213> ORGANISM: Artificial sequence
<220> FEATURE:
<223> OTHER INFORMATION: 6C6 CDR L1

<400> SEQUENCE: 7

Arg Ser Ser Gln Ser Ile Val His Ser Asn Gly Asn Thr Phe Leu Glu
1               5                   10                  15

Trp

<210> SEQ ID NO 8
<211> LENGTH: 8
<212> TYPE: PRT
<213> ORGANISM: Artificial sequence
<220> FEATURE:
<223> OTHER INFORMATION: 6C6 CDR L2

<400> SEQUENCE: 8

Tyr Lys Val Ser Asn Arg Phe Ser
1               5

<210> SEQ ID NO 9
<211> LENGTH: 9
<212> TYPE: PRT
<213> ORGANISM: Artificial sequence
<220> FEATURE:
<223> OTHER INFORMATION: 6C6 CDR L3

<400> SEQUENCE: 9

Phe Gln Ala Ser His Val Pro Pro Thr
1               5

<210> SEQ ID NO 10
<211> LENGTH: 5
<212> TYPE: PRT
<213> ORGANISM: Artificial sequence
<220> FEATURE:
<223> OTHER INFORMATION: 6C6 CDR H1

<400> SEQUENCE: 10

Thr Tyr Asp Met Ser
1               5

<210> SEQ ID NO 11
<211> LENGTH: 18
<212> TYPE: PRT

```
<213> ORGANISM: Artificial sequence
<220> FEATURE:
<223> OTHER INFORMATION: 6C6 CDR H2

<400> SEQUENCE: 11

Thr Ile Ser Ser Gly Gly Ser Tyr Thr Tyr Tyr Pro Asp Ser Val Lys
1               5                   10                  15
Gly Arg

<210> SEQ ID NO 12
<211> LENGTH: 10
<212> TYPE: PRT
<213> ORGANISM: Artificial sequence
<220> FEATURE:
<223> OTHER INFORMATION: 6C6 CDR H3

<400> SEQUENCE: 12

Arg Phe Arg Tyr Asp Gly Trp Tyr Phe Asp
1               5                   10

<210> SEQ ID NO 13
<211> LENGTH: 51
<212> TYPE: DNA
<213> ORGANISM: Artificial sequence
<220> FEATURE:
<223> OTHER INFORMATION: 6C6 CDR L1 coding sequence

<400> SEQUENCE: 13
agatctagtc agagcattgt acatagtaat ggaaacacct ttttagaatg g          51

<210> SEQ ID NO 14
<211> LENGTH: 24
<212> TYPE: DNA
<213> ORGANISM: Artificial sequence
<220> FEATURE:
<223> OTHER INFORMATION: 6C6 CDR L2 coding sequence

<400> SEQUENCE: 14
tacaaagttt ccaaccgatt ttct                                         24

<210> SEQ ID NO 15
<211> LENGTH: 27
<212> TYPE: DNA
<213> ORGANISM: Artificial sequence
<220> FEATURE:
<223> OTHER INFORMATION: 6C6 CDR L3 coding sequence

<400> SEQUENCE: 15
tttcaagctt cacatgttcc tcccacg                                      27

<210> SEQ ID NO 16
<211> LENGTH: 15
<212> TYPE: DNA
<213> ORGANISM: Artificial sequence
<220> FEATURE:
<223> OTHER INFORMATION: 6C6 CDR H1 coding sequence

<400> SEQUENCE: 16
acctatgaca tgtct                                                   15

<210> SEQ ID NO 17
<211> LENGTH: 54
<212> TYPE: DNA
<213> ORGANISM: Artificial sequence
<220> FEATURE:
<223> OTHER INFORMATION: 6C6 CDR H2 coding sequence
```

```
<400> SEQUENCE: 17
accattagta gtggtggtag ttacacctac tatccagaca gtgtgaaggg ccga        54

<210> SEQ ID NO 18
<211> LENGTH: 30
<212> TYPE: DNA
<213> ORGANISM: Artificial sequence
<220> FEATURE:
<223> OTHER INFORMATION: 6C6 CDR H3 coding sequence

<400> SEQUENCE: 18
agatttaggt acgacggctg gtacttcgat        30
```

ANTIBODIES AND PHARMACEUTICAL COMPOSITIONS CONTAINING SAME USEFUL FOR INHIBITING ACTIVITY OF METALLOPROTEINS

RELATED APPLICATIONS

This application is a National Phase Application of PCT Patent Application No. PCT/IL2008/000230 having International Filing Date of Feb. 21, 2008, which claims priority from U.S. Provisional Patent Application No. 60/902,854, filed on Feb. 23, 2007. The contents of the above Application are all incorporated herein by reference.

FIELD AND BACKGROUND OF THE INVENTION

The present invention relates to hapten molecules and antibodies directed thereagainst, which can be used to inhibit activity of metalloproteins, such as metalloproteases, and to methods which utilize the antibodies for treating diseases such as metastatic cancer which are associated with abnormal activity of a metalloprotein.

The matrix metalloproteins (MMPs) are key enzymes participating in remodeling of the extracellular matrix (ECM). These enzymes are capable of destroying a variety of connective tissue components of articular cartilage or basement membranes.

The human MMP gene family consists of at least 28 structurally related proteins (see FIG. 1), which share a similar overall spherical topology (FIG. 2 and Borkakoti, 1998). Each MMP is secreted as an inactive, latent pro-enzyme. The catalytic zinc domain is composed of about 180 amino acids wherein the highly conserved sequence HE-GH-LGL-H provides the three histidine (i.e., H) residues which bind to the metal Zn(2+) ion. The forth-binding site of the catalytic zinc ion in the pro-enzyme is bound to a cystein residue (Morgunova et al., 1999), which upon enzyme activation dissociates from the active site (Van Wart and Birkedal-Hansen, 1990). As a result, the forth-binding site in the activated MMPs is taken up by a water molecule, which is also hydrogen-bonded to a conserved glutamic residue. This process facilitates the hydrolysis of a peptide bond of the target substrate with the activated water molecule.

The uncontrolled breakdown of connective tissue by metalloproteases is a feature of many pathological conditions, probably resulting from an excess of MMP activity or from an imbalanced ratio between the natural MMP tissue inhibitors (TIMPs) and MMPs. TIMPs inhibit MMPs by forming stoichiometric complexes with the active zinc binding site of MMPs (Gomez et al., 1997; Henriet at al., 1999; Bode et al., 1999; Will et al., 1996). When TIMPs levels are insufficient, a progressive slow degradation of the ECM may lead to loss of cartilage matrix in rheumatoid arthritis (Walakovits et al., Arthritis Rheum, 35:35-42, 1992) and osteoarthritis (Dean et al., J. Clin. Invest. 84:678-685, 1989) or bone matrix degradation in osteoporosis (Hill et al., Biochem. J. 308: 167-175, 1995). In other situations, such as congestive heart failure, rapid degradation of the heart's ECM may occur (Armstrong et al., Canadian J. Cardiol. 10: 214-220, 1994).

Additionally, MMPs are known to play a role in the maturation of cytokines and chemokines such as galectin-3 (Ochieng J., Biochemistry, 1994 33(47):14109-14), plasminogen (Patterson, BC., JBC, 1997 272(46):28823-5, interleukin-8, connective tissue activating peptide III, platelet factor-4 (Van den Steen, 2000 Blood. 2000 Oct. 15;96(8):2673-81.), pro-interleukin-1β (Schonbeck, 1998), interleukin-2 receptor α chain [Sheu, B. C, Hsu, S. M., Ho, H., Lien, H. C., Huang, S. C., Lin, R. H. A novel role of metalloproteinase in cancer-mediated immunosuppression *Cancer Research* (2001) 61, 237-242], and pro-transforming growth factor-β [TGF-β, Yu, Q. Stamenkovic, I. Cell surface-localized matrix metalloproteinase-9 proteolytically activates TGF-beta and promotes tumor invasion and angiogenesis *Genes Dev* (2000) 14, 163-176].

Other pathological conditions, which are also related to unregulated activity of MMPs, include the rapid remodeling of the ECM by metastatic tumor cells. In such conditions the activated MMPs are either expressed by the cancer cells or by the surrounding tissues. There is considerable evidence that MMPs are involved in the growth and spread of tumors (e.g., see Davidson et al., Chemistry & Industry, 258-261, 1997, and references therein). In the process of tumor metastasis, MMPs are used to break down the ECM, allowing primary tumor cancer cells to invade neighboring blood vessels where they are transported to different organs and establish secondary tumors. The invasive growth at these secondary sites is mediated by MMPs, which break down the tissue. In addition, MMP activity contributes to the invasive in-growth of new blood vessels, also termed angiogenesis, which is required for tumors to grow above a certain size. Among the members of MMP family, the secreted human MMP-9, also known as gelatinase B, has been shown to have key roles not only in extracellular matrix (ECM) catabolism but also in the processing of protein substrates that are relevant in neurological diseases such as multiple sclerosis (MS) (Opdenakker, 2003). Recent studies showed that MMP-9 has a critical role in promoting autoimmune diseases by cleaving pre-processed type II collagen (Van den Steen, 2004). The products are collagen type II fragments that are remnant epitopes thought to generate autoimmune diseases.

Given the broad role of MMPs in human physiology and pathology, it is not surprising that numerous efforts have been affected to design drugs, which inhibit MMP excessive activity.

Drug discovery efforts have focused on inhibitor classes that contain a functional group which coordinates the zinc ion to thereby inactivate the target MMP. One such inhibitor class is the hydroxamate inhibitors, small peptide analogs of fibrillar collagens, which specifically interact in a bidentate manner via the hydroxyl and carbonyl oxygens of the hydroxamate group with the zinc ion in the catalytic site [Grams et al., (1995), Biochem. 34: 14012-14020; Bode et al., (1994), EMBO J., 13: 1263-1269].

Hydroxamate-based MMP inhibitors are usually composed of either a carbon back-bone (WO 95/29892, WO 97/24117, WO 97/49679 and EP 0780386), a peptidyl back-bone (WO 90/05719, WO 93/20047, WO 95/09841 and WO 96/06074) or a peptidomimetic back-bone [Schwartz et al., Progr. Med. Chem., 29: 271-334(1992); Rasmussen et al., Pharmacol. Ther., 75: 69-75 (1997); Denis et al., Invest. New Drugs, 15: 175-185 (1997)]. Alternatively, they contain a sulfonamido sulfonyl group which is bonded on one side to a phenyl ring and a sulfonamido nitrogen which is bonded to an hydroxamate group via a chain of one to four carbon atoms (EP 0757984 A1).

Other peptide-based MMP inhibitors are thiol amides which exhibit collagenase inhibition activity (U.S. Pat. No. 4,595,700), N-carboxyalkyl derivatives containing a biphenylethylglycine which inhibit MMP-3, MMP-2 and collagenase (Durette, et al., WO-9529689), lactam derivatives which inhibit MMPs, TNF-alpha and aggrecanase (see U.S. Pat. No. 6,495,699) and Tricyclic sulfonamide compounds (see U.S. Pat. No. 6,492,422).

Although peptide-based MMP inhibitors have a clear therapeutic potential their use in clinical therapy is limited. Peptide-based hydroxamate are costly to produce and have low metabolic stability and oral bioavailability [e.g., batimastat (BB-94)]. These compounds are rapidly glucuronidated, oxidized to carboxylic acid and excreted in the bile [Singh et al., Bioorg. Med. Chem. Lett. 5: 337-342, 1995; Hodgson, "Remodelling MMPIs", Biotechnology 13: 554-557, 1995)]. In addition, peptide-based MMP inhibitors often exhibit the same or similar inhibitory effects against each of the MMP enzymes. For example, batimastat is reported to exhibit $IC_{50}$ values of about 1 to about 20 nM against each of MMP-1, MMP-2, MMP-3, MMP-7, and MMP-9 [Rasmussen et al., Pharmacol. Ther., 75(1): 69-75 (1997)]. Furthermore, the use of several hydroxamate inhibitors was associated with severe side effects such as muscoloskeletal problems with marimastat (BB-2516), widespread maculopapular rash with CGS27023A (Novartis) [Levitt et al., 2001, Clin. Cancer Res. 7: 1912-1922] and liver abnormalities, anemia, shoulder and back pain, thrombocytopenia, nausea, fatigue, diarrhea and deep vein thrombosis with BAY12-9566 (Bayer) [Heath et al., 2001, Cancer Chemother. Pharmacol. 48: 269-274]. Moreover, phase III clinical trials on advanced cancer patients with marimastat, prinomastat (AG 3340, Agouron) and Bay 12-9566 demonstrated no clinical efficacy in inhibiting metastasis (Zucker et al., 2000, Oncogene 19: 6642-50).

Other MMP inhibitors are the chemically modified nonmicrobial tetracyclines (CMTs) that were shown to block expression of several MMPs in vitro. However, in vivo efficacy of these compounds was found to be limited, e.g., the CMT inhibitor, doxycycline, reduced tissue levels of MMP-1 but not MMP-2, 3, or -9 in atherosclerotic carotid plaques in human patients (Axisa et al., 2002, Stroke 33: 2858-2864).

Recently, a mechanism-based MMP inhibitor, SB-3CT, was designed according to the X-ray crystallographic information of the MMP active site (Brown et al., 2000). X-ray absorption studies revealed that binding of this molecule to the catalytic zinc reconstructs the conformational environment around the active site metal ion back to that of the pro-enzyme [Kleifeld et al., 2001, J Biol. Chem. 276: 17125-31]. However, the therapeutic efficacy obtained with this agent is yet to be determined.

Another class of natural inhibitors is monoclonal antibodies. Several antibodies have been raised against specific peptide sequences within the catalytic domain MMP-1 (Galvez et al., 2001, J. Biol. Chem., 276: 37491-37500). However, although these antibodies could inhibit the in-vitro activity of MMP, results demonstrating the in-vivo effectiveness of such antibodies have not been demonstrated.

As described hereinabove, the catalytic site of MMPs includes a coordinated metal ion which becomes available for substrate binding following enzyme activation (see FIGS. 2a-c). It is thus conceivable that conventional antibodies directed at the primary amino acid sequence of the enzyme would not distinguish the active form from the inactive form of the enzyme and hence would not serve as potent inhibitors of such enzymes.

The present inventors have previously shown that antibodies which recognize both electronic and structural determinants of the catalytic site of MMPs are potent inhibitors thereof and as such can be used to treat diseases associated with imbalanced MMP activity (see PCT Publication WO 2004/087042).

There is thus, a widely recognized need for and it would be highly desirable to have specific hapten compounds which mimic the electronic and structural determinants of the catalytic site of metalloproteins as well as specific antibodies which are directed thereagainst.

SUMMARY OF THE INVENTION

According to one aspect of the present invention there is provided a compound having the general Formula (I):

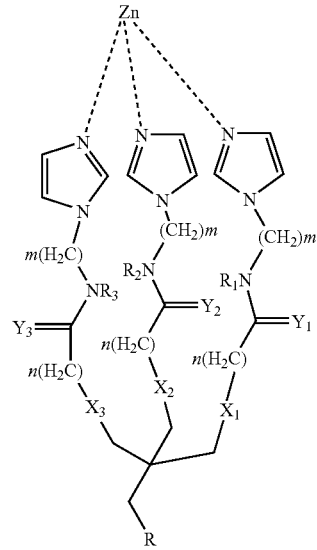

wherein:
m and n are each independently an integer from 1 to 6;
$X_1$-$X_3$ and $Y_1$-$Y_3$ are each independently O or S;
$R_1$-$R_3$ are each indepdnently selected from the group consisting of hydrogen, alkyl, and cycloalkyl; and
R is $(CH_2)x$-$C(=O)NR'$—$(CH_2)y$-$NR'R''$
whereas:
x and y are each independently an integer from 1 to 6; and
R' and R'' are each independently selected from the group consisting of hydrogen, alkyl, and cycloalkyl.

According to further features in preferred embodiments of the invention described below, the compound has the Formula (II):

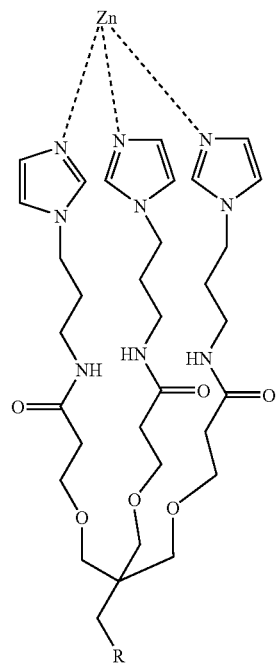

wherein R=—$CH_2$—$C(=O)NH$—$CH_2$—$CH_2$—$NH_2$

According to another aspect of the present invention there is provided a compound having the Formula (II):

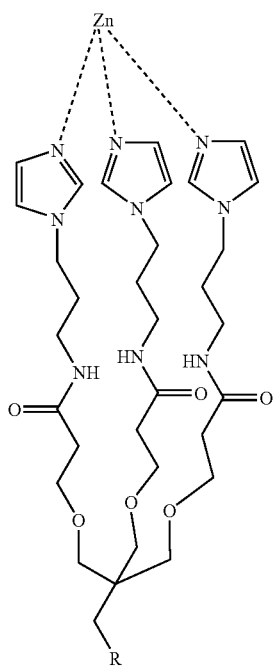

wherein R=—CH$_2$—C(=O)NH—CH$_2$—CH$_2$—NH$_2$

According to yet another aspect of the present invention there is provided an antibody comprising an antigen recognition region capable of specifically binding the above compound.

According to still further features in the described preferred embodiments the antigen recognition region comprises a CDR amino acid sequence selected from the group consisting of SEQ ID NO: 7, 8, 9, 10, 11 and 12.

According to still further features in the described preferred embodiments the CDR amino acid sequence is encoded by a nucleic acid sequence selected from the group consisting of SEQ ID NO: 13, 14, 15, 16, 17 and 18.

According to still further features in the described preferred embodiments the antibody is capable of inhibiting an activity of a metalloproein.

According to still further features in the described preferred embodiments the metalloprotein is a matrix metalloprotease.

According to still further features in the described preferred embodiments the matrix metalloprotease is a gelatinase.

According to still further features in the described preferred embodiments the gelatinase is selected from the group of MMP-2 and MMP-9.

According to still another aspect of the present invention there is provided a method of producing a metalloprotein inhibitor, the method comprising generating antibodies directed at the above compound, thereby producing the metalloprotein inhibitor.

According to still further features in the described preferred embodiments the antibodies are polyclonal antibodies.

According to still further features in the described preferred embodiments the antibodies are monoclonal antibodies.

According to an additional aspect of the present invention there is provided a pharmaceutical composition comprising the antibody and a pharmaceutically acceptable carrier.

According to an additional aspect of the present invention there is provided a method of treating a disease associated with imbalanced or abnormal activity of metalloproteins in a subject in need thereof, the method comprising administering to the subject a therapeutically effective amount of the lantibody claimed herein thereby treating a disease associate with imbalanced or abnormal activity of metalloproteins in the subject.

According to still further features in the described preferred embodiments the disease is an inflammatory bowel disease.

According to an additional aspect of the present invention there is provided a method of inhibiting matrix metalloprotease activity in a cell, the method comprising contacting the cell with the antibody claimed herein, thereby inhibiting the matrix metalloprotease activity in the cell.

The present invention successfully addresses the shortcomings of the presently known configurations by providing a novel hapten composition which can be used to generate antibodies which recognize both electronic and structural determinants of the catalytic site of metalloproteins.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. In case of conflict, the patent specification, including definitions, will control. In addition, the materials, methods, and examples are illustrative only and not intended to be limiting.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The invention is herein described, by way of example only, with reference to the accompanying drawings. With specific reference now to the drawings in detail, it is stressed that the particulars shown are by way of example and for purposes of illustrative discussion of the preferred embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

In the drawings:

Figure 1A:
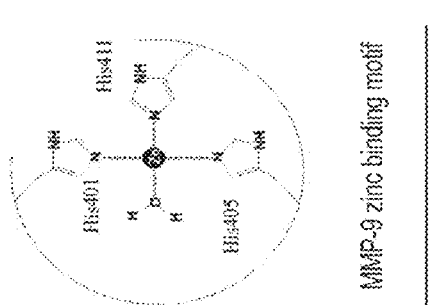
Figure 1B:
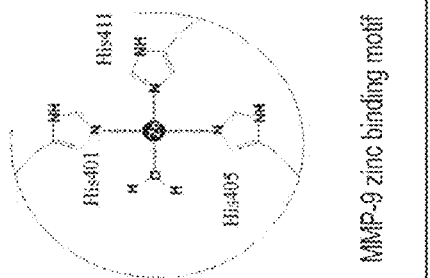
Figure 1C:
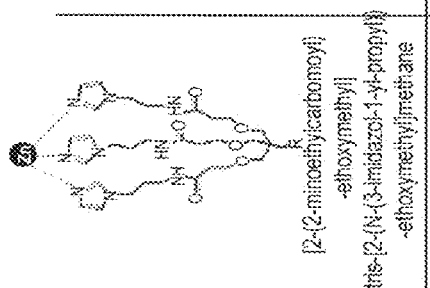
Figure 1D:
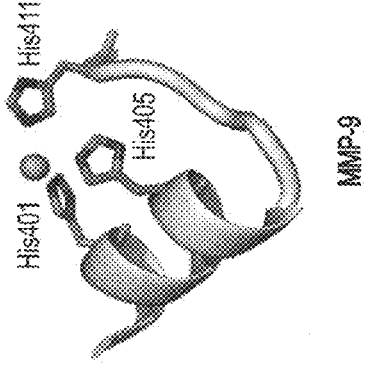
Figure 1E:
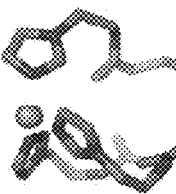
Figure 1F:
Figure 1G:
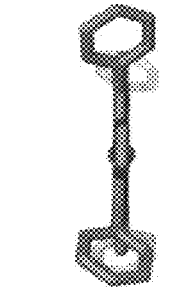
Figure 1H:
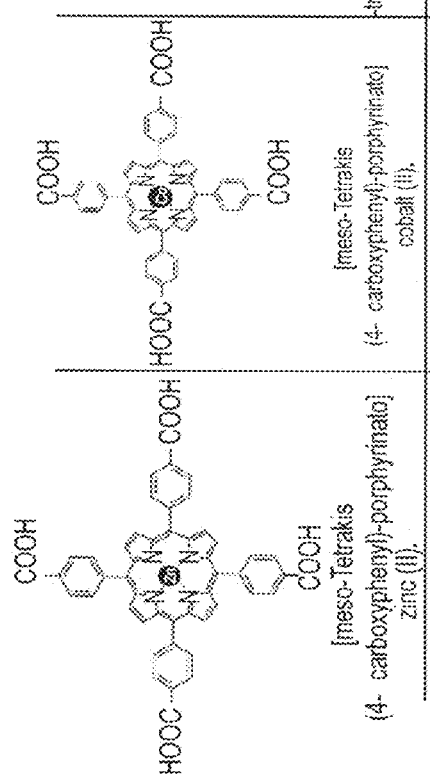

FIGS. 1A-D are schematic representations of the molecular structure of Co/ZnTCPP—[meso-Tetrakis (4-carboxyphenyl)-porphyrinato] cobalt/zinc (II) (FIGS. 1A-B, Imi-sdp—[2-(2-minoethylcarbomoyl)-ethoxymethyl]-tris-[2-(N-(3-imidazol-1-yl-propyl))-ethoxymethyl]methane, and the conserved zinc-protein ligation at the catalytic zinc site in MMPs.

FIGS. 1E-H are three dimensional schemes of the structures displayed in FIGS. 1A-d. Note, the ZnTCPP retains planar conformation while the CoTCPP exhibit a distorted microcycle conformation. Remarkably, the misdp structure is highly analogous to the nearest environment of the catalytic zinc ion in MMP-9 as demonstrated in FIG. 1G.

FIG. 2A is a structural overlay between the three dimensional calculated structures of Imisdp (green carbon atoms) and the three conserved histidines at the active site of MMP-9 (PDB code 1GKC, grey carbon atoms). The catalytic zinc ion is depicted as an orange ball, water molecule is depicted as a blue ball, nitrogens are colored blue, oxygens red.

FIG. 2B is a structural overlay between ZnTCPP porphyrinic ring (CSD code AKICOM) (green carbon atoms) and the three conserved histidines at the active site of MMP-9 (grey carbon atoms PDB code 1GKC), the catalytic zinc ion is depicted as an orange ball, nitrogens are colored blue FIGS. 3A-C are western blot images showing the ability of mouse IgG—Agarose immobilized mAbs to pull down recombinant MMP-2 catalytic domain (MMP-2cat) or Pro-MMP-2 and Pro-MMP-9 from solution. Antibodies used for each experiment are 6C6, 13E11, and 13E15. FIG. 3A—MMP-2cat (2 µg) was incubated with anti-mouse IgG—Agarose (cnt1, lane1) or anti CoTCPP, ZnTCPP and Imisdp mAb (10 µg)-anti-mouse IgG—Agarose for 2 hr at 20° C., immunoprecipitates (lane 2,3,5) were centrifuged and washed three times, separated on SDS/PAGE gel and visualized by Coomassie-staining. FIG. 3B—Pro-MMP-2, Pro-MMP-9 were incubated with mAbs-anti-mouse IgG—Agarose in the same manner as in A. Immunoprecipitates (lane 2,4,6 left and 1,3,5 right) and unbound fraction (lane 1,3,5 left and 2,4,6 right) were separated on SDS/PAGE gel and visualized by Coomassie-staining. FIG. 3C—conditioned medium of HT1080 cells that either underwent activation with APMA (left) or did not (right), was immunoprecipitated with anti CoTCPP mAb and analyzed by western blot with specific antibodies against MMP-2.

FIGS. 4A-B are Lineweaver-Burk plots of anti CoTCPP mAb inhibition of MMP-2 (A) and MMP-9 (B). Velocity units are in uniol/sec$^{-1}$, and substrate units are in FIG. 4A—MAb concentrations were 6 (closed triangles), 18 (closed squares), 24 (open circles), and 0 µM (open squares). MMP-2cat concentration was 200 nM. FIG. 4B—Inhibition of full length APMA activated MMP-9, mAb concentrations were 6 (open squares), 12 (closed triangles), 24 (open squares), and 0 µM (closed squares). MMP-9 concentration was 20 nM. The inhibition pattern indicates that anti CoTCPP mAb behaves as a competitive inhibitor of MMP-2 and MMP-9.

Figure 5:
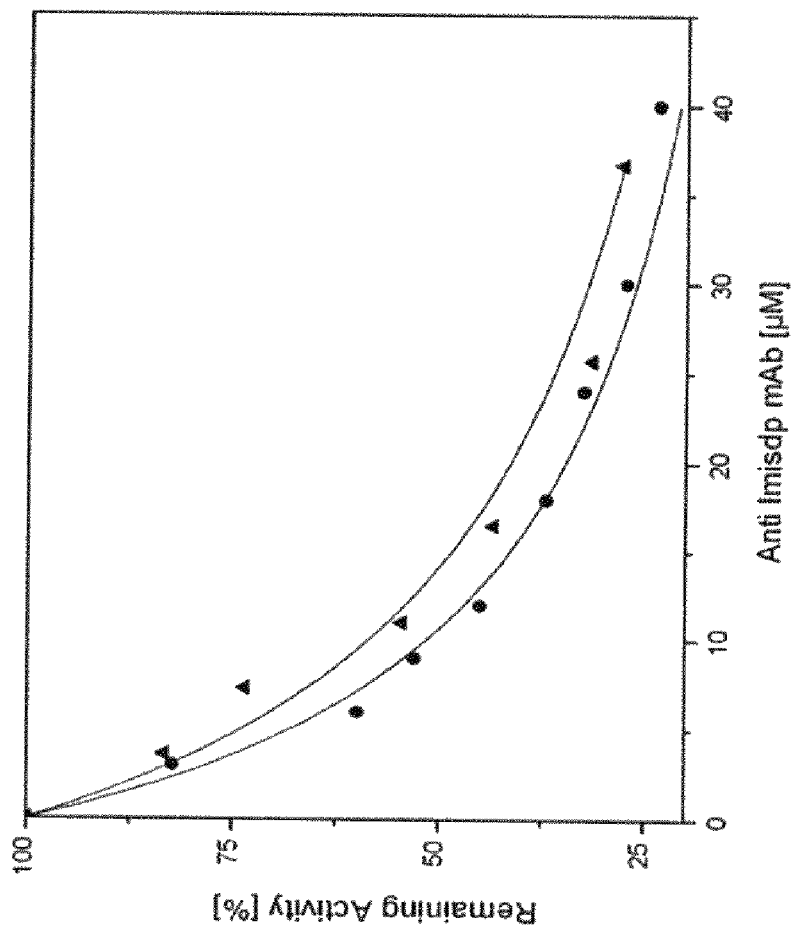

FIG. 5 is a plot showing MMP-2 and MMP-9 inhibition by anti Imisdp mAb. MMP-9 catalytic domain (20 nM) (closed circles) or full length APMA activated MMP-2 (closed triangles, 5 nM) was added to mixtures of the fluorogenic substrate OCAcPLGLA2pr(Dnp)-AR-NH2 (10 µM) in buffer R containing increasing concentrations of mAb.

The lines represent nonlinear least-squares fits to the Equation:

$$vi/v=(Km+[S])/(Km(1+[I]/Ki)+[S]),\text{ using the program Origin.}$$

Figure 6A:
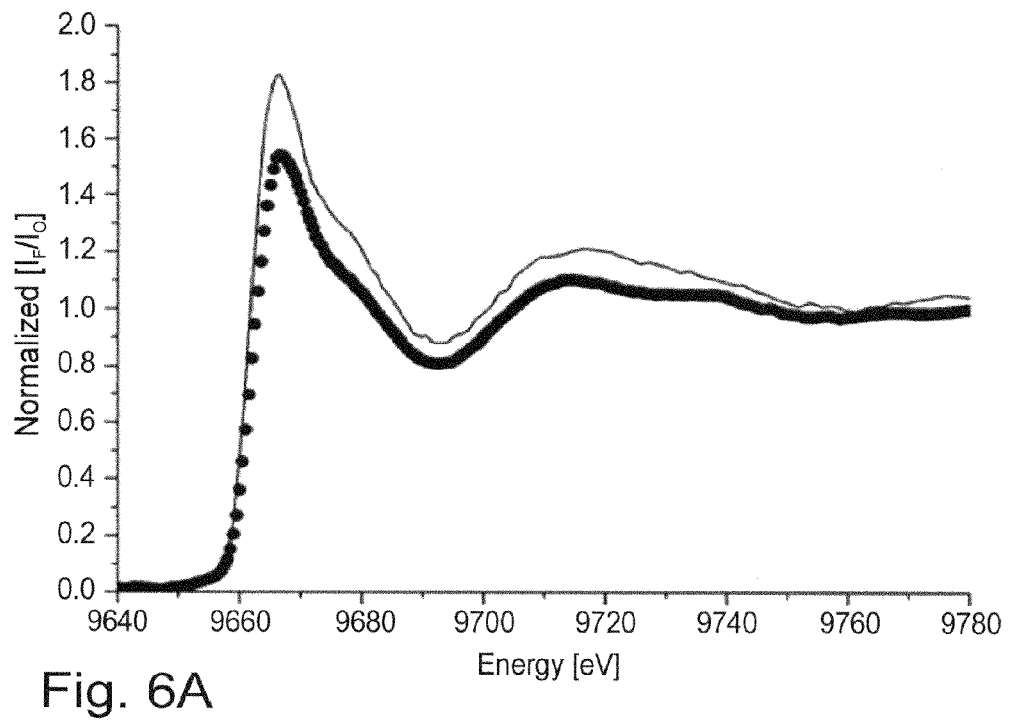

FIG. 6A shows zinc k-edge spectra of active and anti CoTCPP mAb inhibited forms of MMP-2cat. Normalized raw XAS data of zinc K-edge region of active (dotted) and MMP-2cat -mAb (solid) complex are shown.

Figure 6B:
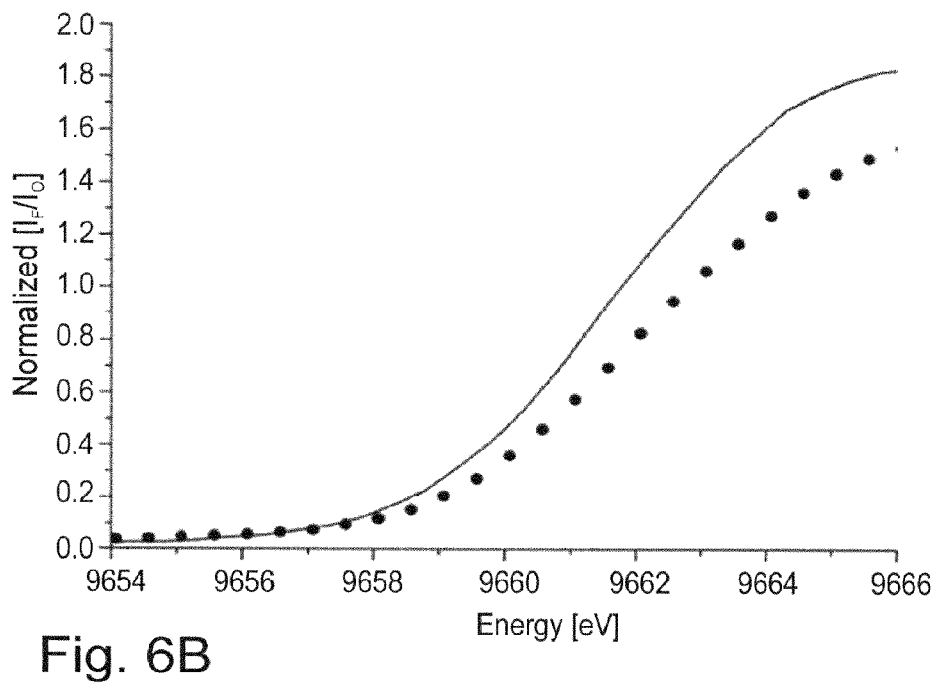

FIG. 6B shows the edge position the MMP-2cat-mAb complex (solid) shifts to a higher energy relative to active MMP-2cat (dotted).

Figure 6C:
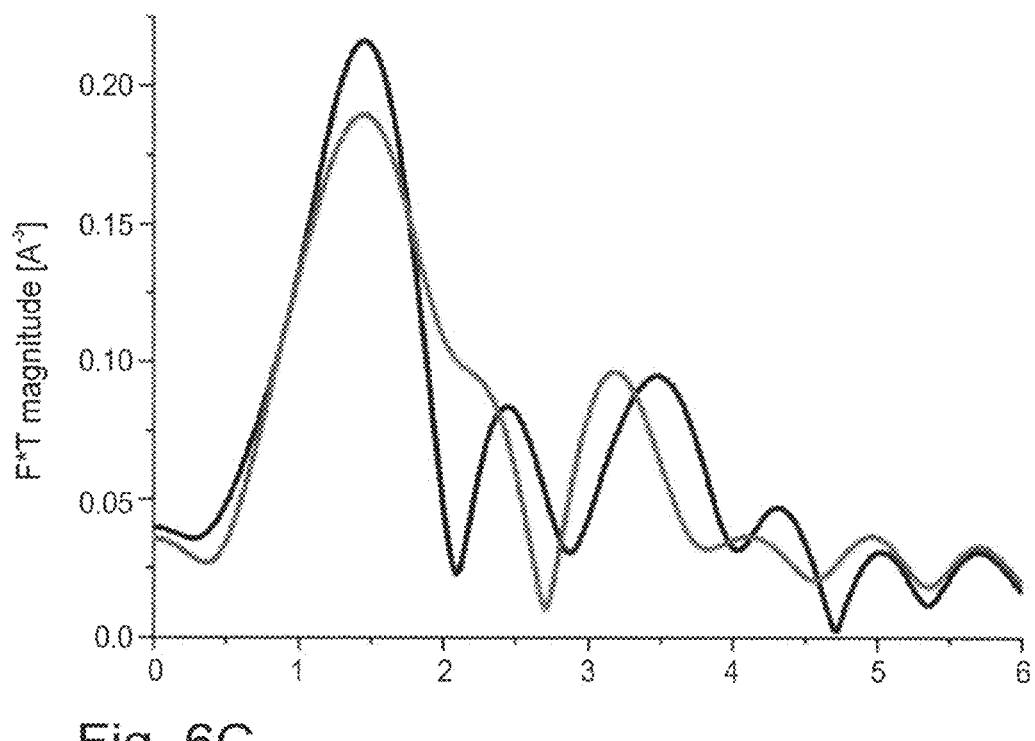

FIG. 6C shows EXAFS results for active (black) and inhibited (green) forms of MMP-2cat are shown. The results are presented in R-space and back-transformed to the k-space.

Figures 7A, 7B:
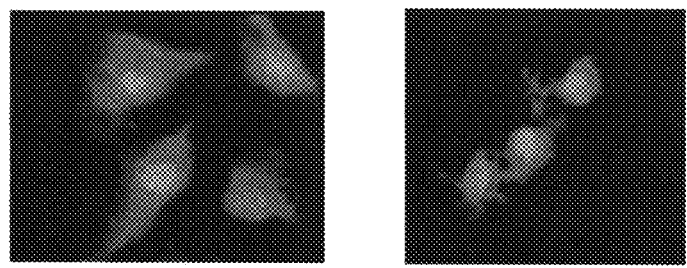

FIGS. 7A-B are photographs showing the ability of anti CoTCPP mAb to inhibit cell surface gelatinase activity. Representative fluorescent micrographs of HT1080 cells plated on cover slips coated with DQ-gelatin in the presence or absence of 1 uM of 13E11 mAb. Cell surface gelatinolytic activity was assayed as a measure of fluorescence emitted by degraded gelatin. Untreated cells exhibited significant cell surface gelatinase activity, which was significantly inhibited in the presence of 1 uM of anti CoTCPP mAb. 4'-6-Diamidino-2-phenylindole (DAPI) staining, in blue, indicates the location of the nuclei of the cells.

Figure 8:
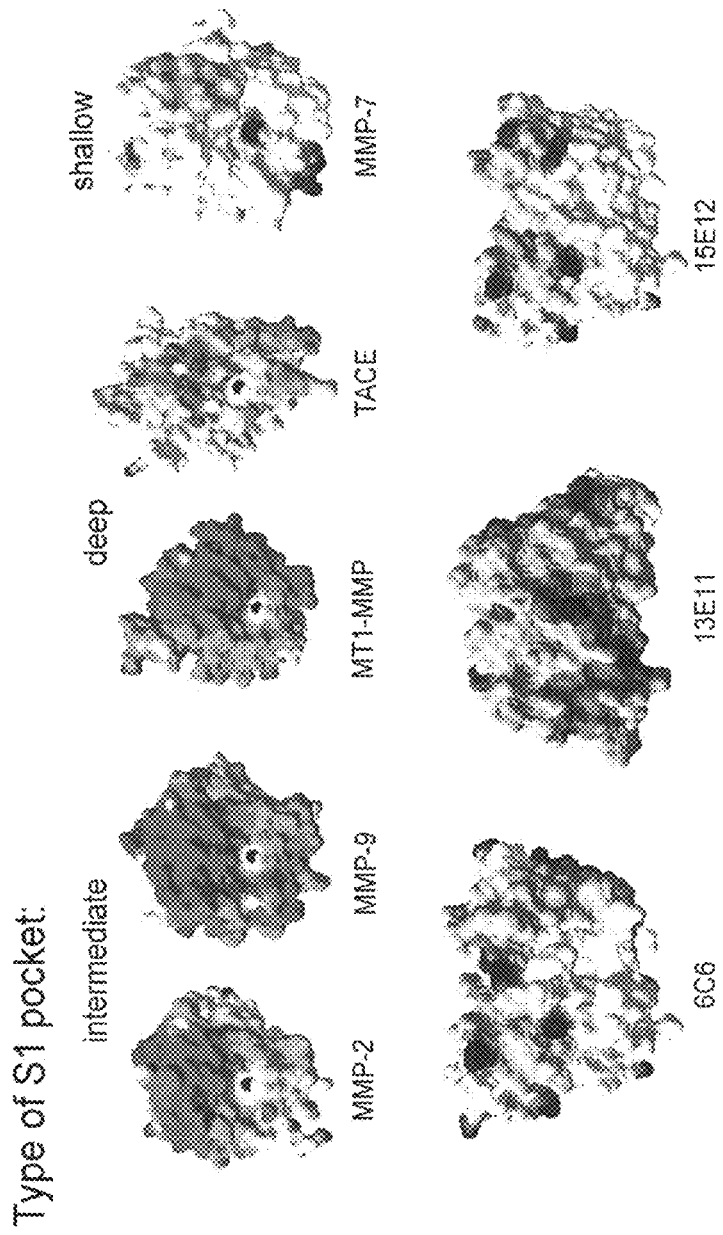

FIG. 8 is a scheme showing the configuration of the various MMP active sites (S1 pocket).

Figure 9:
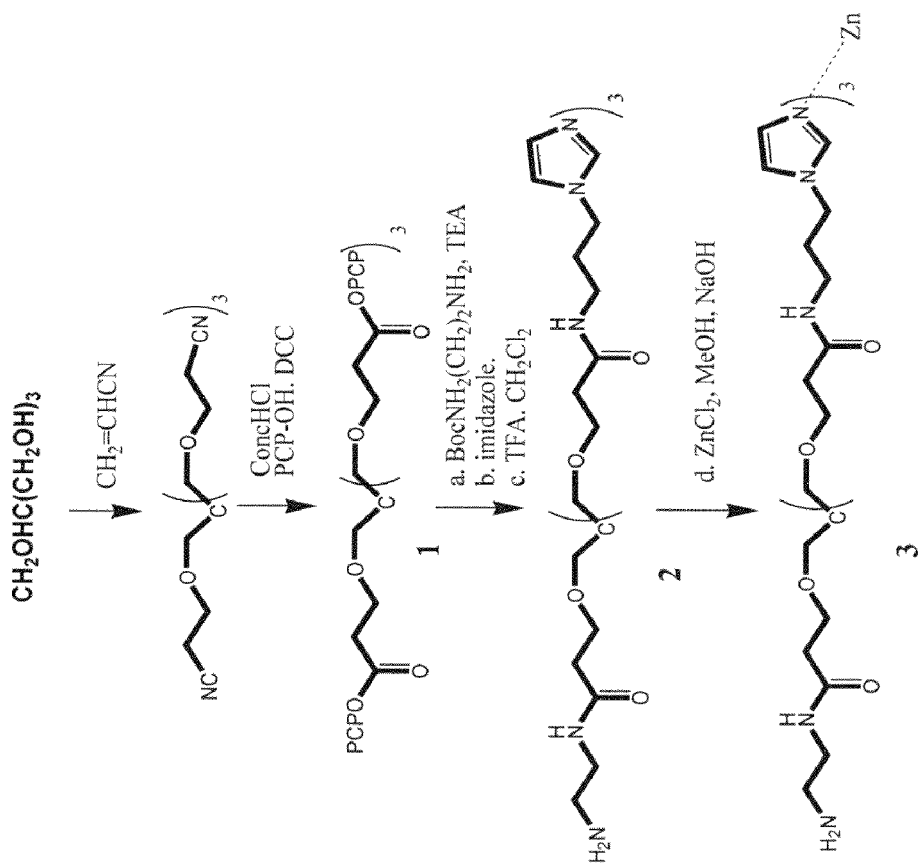

FIG. 9 is the Imisdp synthesis scheme.

FIG. 10 shows the amino acid sequences of the antibodies of the present invention with CDR regions highlighted.

FIGS. 11A-D are photographs and models illustrating that 6C6 binds only the active conformation of MMP9 and MMP2. FIG. 11A: Detection of active MMP9 that co-purified with 6C6 from mice ascites fluid. MAb (10 µg) purified from mice ascites fluid containing MMP9, was subjected to western blot (WB) analysis using commercial anti MMP9 antibody. Non related IgG mAb that has been purified in the same manner, served as negative control (MAb Control). Human ProMMP9 purified from Hilla transfected cells served as molecular weight marker to discern the active species. Purification was done by affinity chromatography using protein G beads which bind mAb via its constant domain, leaving the antigen binding site free to interact with the antigen. FIGS. 11B,C: 6C6 mAb immobilized to protein A beads was analyzed for its ability to pull down ProMMP2, ProMMP9, or MMP2 catalytic fragment (lacking the hemopexin and pro domains) from solution. MAbs 6C6 (10 µg) immobilized to protein A Sepharose beads was incubated with MMP2 catalytic fragment (1 µg)—FIG. 11B, ProMMP9—FIG. 11C top, or ProMMP2 (2 µg) (FIG. 11C bottom, for 2 hours at 20° C. Bead-bound mAb complex was separated by centrifugation and washed three times, separated on SDS/PAGE gel and visualized by Coomassie-staining. Immunoprecipitates (6C6) and unbound fractions were separated on SDS/PAGE gel and visualized by Coomassie-staining. As negative control for non specific adsorption enzyme alone was incubated with protein A Sepharose beads. FIG. 11D: The three-dimensional structure of MMP2 lacking the hemopexin domain with (bottom) and without (top) the pro-domain is shown in surface representation (PDB ID: 1CK7). The catalytic and the fibronectin domains are shown in cyan and pro-peptide in red. The catalytic zinc ion is depicted as an orange sphere and bound to three conserved histidines shown as yellow sticks. As shown the pro-peptide domain sterically blocks the active site.

FIGS. 12A-B are graphs and data relating to the inhibition mechanism of MMP-9 by 6C6 mAb. FIG. 12A: MMP-9 recombinant catalytic fragment (without the hemopexin and pro domain) was preincubated with varying amounts of mAb. The residual enzymatic activity was measured after addition of fluorogenic peptide substrate (10 µM). Ki was evaluated by fitting to equation of competitive inhibition (vi/vo=Km+[S]/(Km(1+I/Ki)+[S]) Km=9.14±0.8) (Inset) Active MMP-9 (at a fixed concentration of 2 nM) was preincubated for 60 minutes at 37° C. in the absence (●) or presence of 0.7 (■) or 2 µM (O) mAb, in 100 mM NaCl, 10 mM CaCl$_2$, 100 mM Tris pH 7.5. Fluorogenic peptide substrate (Mca-Pro-Leu-Gly-Leu-Dpa-Ala-Arg-NH2) was then added to achieve the final concentrations indicated (S) in the range of 0-30 µM, and the initial velocity of substrate hydrolysis was determined by measurement of increased fluorescence. The values of apparent Km and Vmax were derived by fitting the experimental data to Michaelis-Menten equation. The derived values were used to reconstruct double reciprocal Linweaver-Burk plot the intersection points indicate competitive inhibition of MMP-9 by 6C6. FIG. 12B: The different MMPs were preincubated with varying amounts of mAb. The residual enzymatic activity was measured after addition of fluorogenic peptide substrate (10 µM). Ki was evaluated by fitting to equation of competitive inhibition (vi/vo=Km+[S]/(Km(1+I/Ki)+[S]) Km=2.46±0.34 for full length MMP2 purified from Hila cells, Km=16±1 for catalytic domain of MT1-MMP). Effective inhibition of 6C6 was also detected using full length MMP-2 and MMP-9 (data are not shown).

Figure 13:
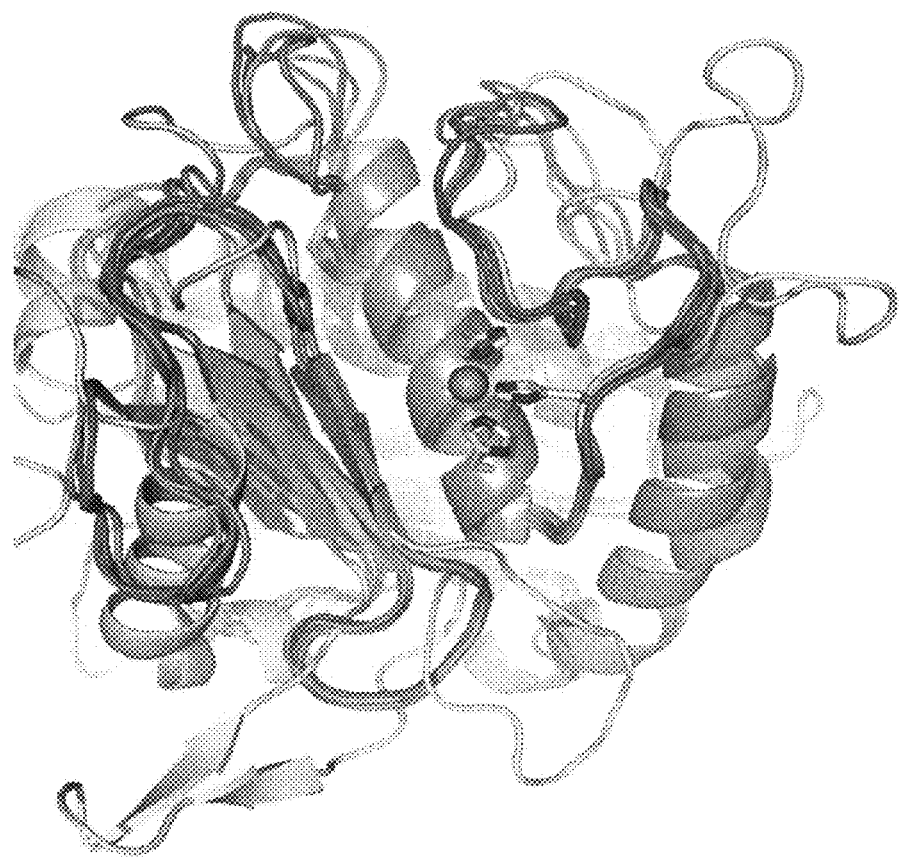

FIG. 13 is a structural overlay of different MMPs showing the conserved overall topology of the active site with variations mostly within the peripheral loops. MMP9 (PDB 1GKC)-cyan, MMP2 (PDB 1QIB)-magenta, MT1-MMP (PDB 1BUV)-orange, MMPI (PDB 1MMQ)-red, TACE (PDB 2147)-yellow. Conserved histidines are shown as sticks, catalytic zinc ion is depicted as orange ball. Remarkably, the overall topography of the peripheral loops of MMP-2 and MMP-9 is similar. This may explain the selectivity of 6C6 to MMP-2 and MMP-9 in the tested group of enzymes.

Figure 14:
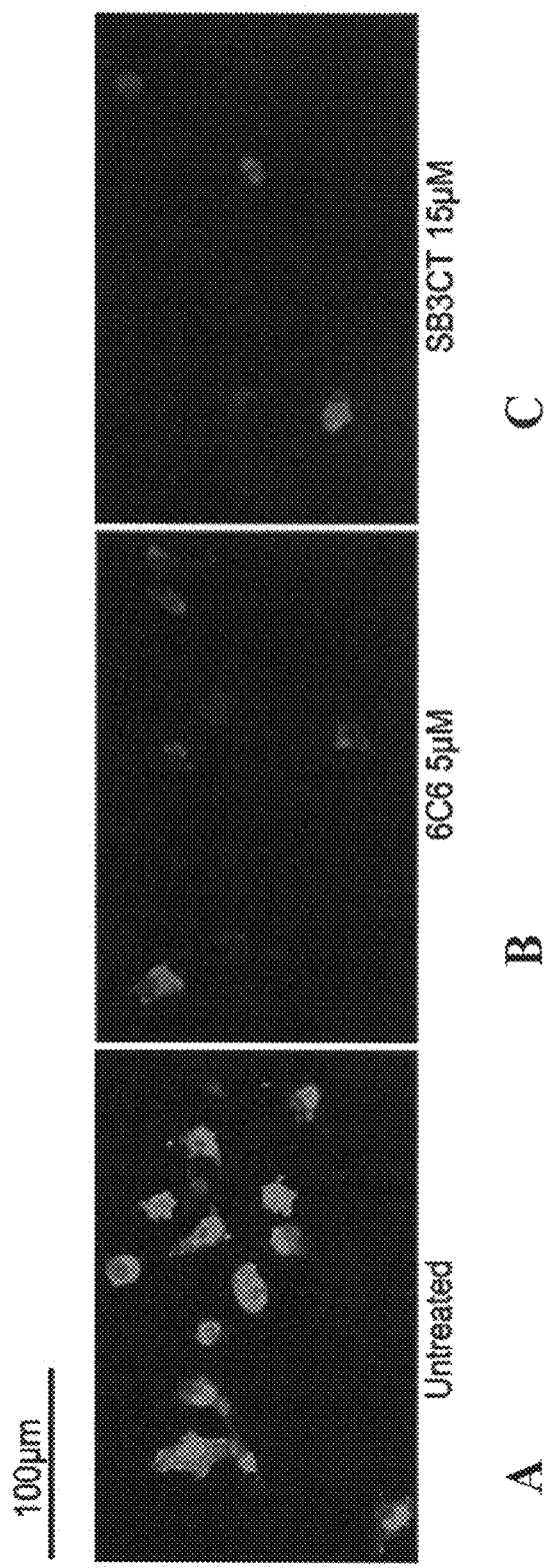

FIGS. 14A-C are fluorescent micrographs illustrating that 6C6 inhibits cell surface gelatinase activity. Representative fluorescent micrographs (generated by in situ zymography assay) of HT1080 cells plated on cover-slips coated with DQ-gelatin in the absence (FIG. 14A) or presence (FIG. 14B) of 5 µM mAb or 15 µM SB-3CT mechanism based nanomolar inhibitor of gelatinases (FIG. 14C). Cell surface gelatinolytic activity was assayed as a measure of fluorescence emitted by degrading gelatin. Untreated cells exhibited significant cell surface gelatinase activity (green), which was significantly inhibited in the presence of mAb.

Figure 15:
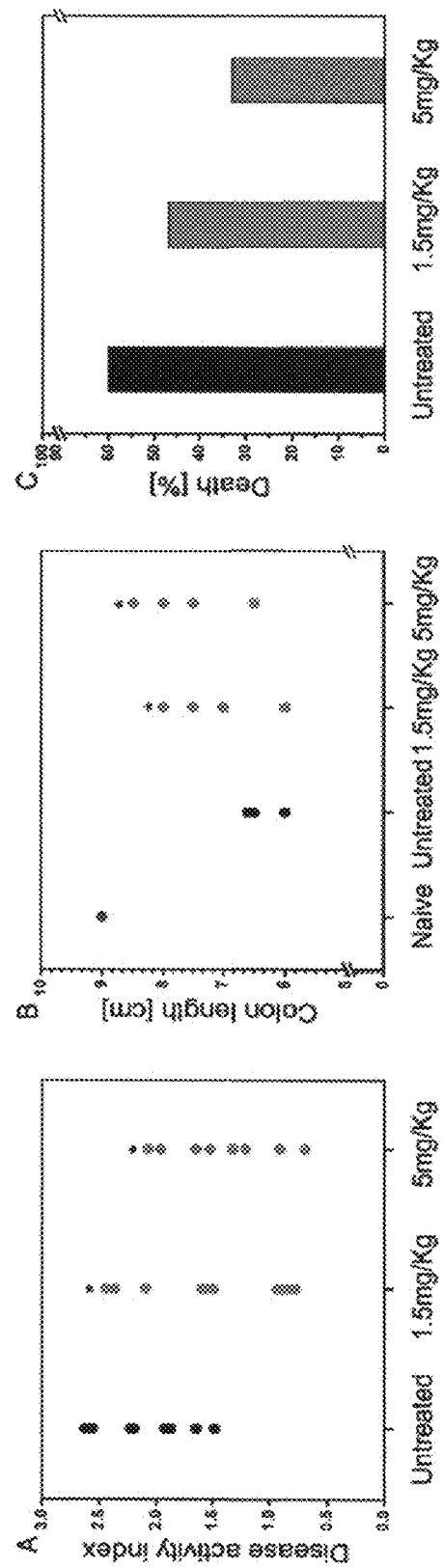

FIGS. 15A-C are graphs illustrating the effect of 6C6 treatment on the various manifestations of acute DSS colitis in C57BL/6 mice. Disease was induced by 2% DSS for 5 days. 6C6 treatment, 5 or 1.5 mg/kg mouse, was administered by daily i.p. injection starting from day 0. FIG. 15A: Clinical score was evaluated by daily monitoring of DAI (which is the combined score of body weight, rectal bleeding and stool consistency, on a scale of 0-4). Data are expressed as the dot distribution of a mean for each animal of days 6 to 10. FIG. 15B: Colon length. FIG. 15C: Mortality. The data presented are the combined results of two experiments, with a total of 15 mice per group.*, significant effect over colitis-untreated mice ($p<0.05$).

Figure 16:
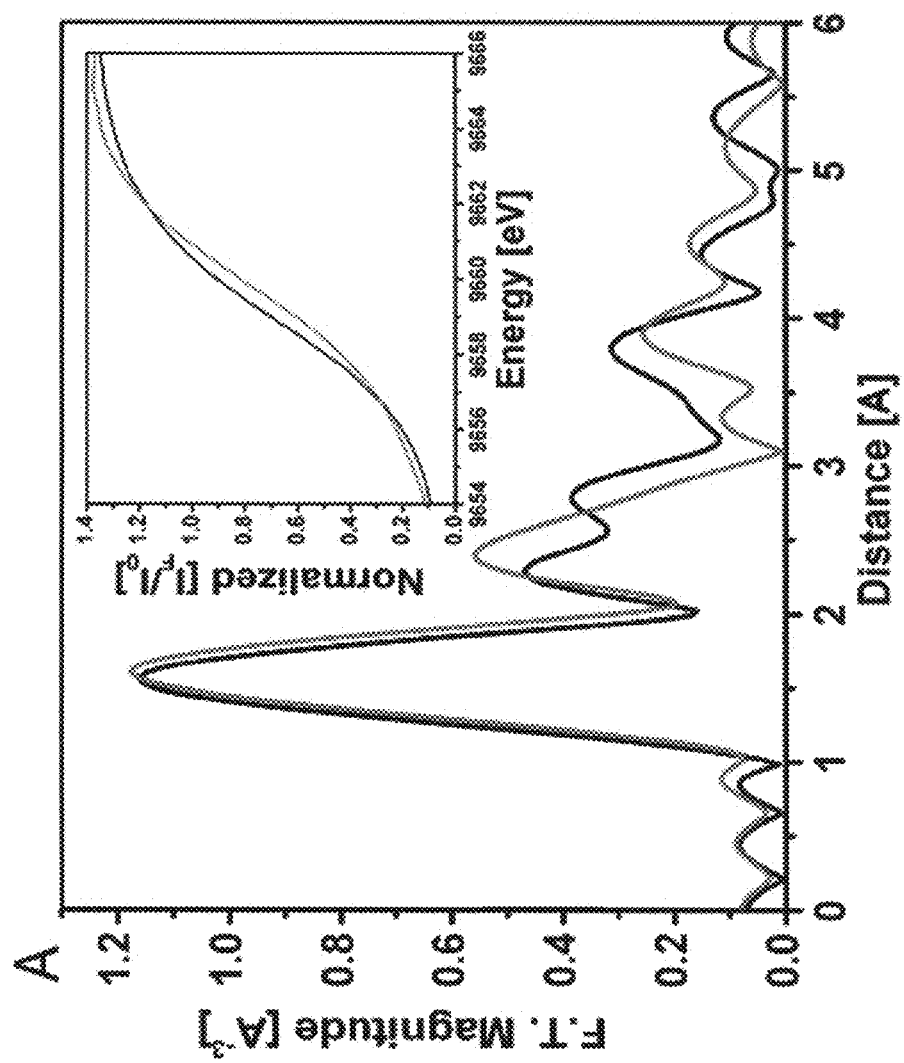

FIG. 16 is a graph of results from X-ray absorption spectroscopy at the zinc K edge of active MMP9 (black) and inhibited MMP9-6C6 complex (red). The results are presented in the form of radial distribution from the zinc ion. The edge position the MMP-9 catalytic domain-mAb complex (red) shifts to a higher energy relative to active MMP-9 (inset) indicating binding to the catalytic zinc ion. Structural analysis of the X-ray spectroscopy data indicates that 6C6 directly binds the zinc ion and forms pentacoordinate zinc-protein complex. Remarkably, this mode of binding is analogous to the binding of TIMPs at the active site of MMPs.

DESCRIPTION OF THE PREFERRED EMBODIMENTS

The present invention is of antibodies and fragments thereof, which can be used to inhibit metalloprotein activity. Specifically, the antibodies of the present invention can be used to treat diseases associated with imbalanced matrix metalloprotease activity such as multiple sclerosis, autoimmune diseases and metastatic cancers.

The principles and operation of the present invention may be better understood with reference to the drawings and accompanying descriptions.

Before explaining at least one embodiment of the invention in detail, it is to be understood that the invention is not limited in its application to the details set forth in the following description or exemplified by the Examples. The invention is capable of other embodiments or of being practiced or carried out in various ways. Also, it is to be understood that the phraseology and terminology employed herein is for the purpose of description and should not be regarded as limiting.

Matrix metalloproteases participate in many biological processes, ranging from cell proliferation, differentiation and remodeling of the extracellular matrix (ECM) to vascularization and cell migration. These processes require a delicate balance between the functions of the matrix metalloproteases (MMPs) and natural tissue inhibitors thereof (TIMPs). The loss of this balance is the hallmark of numerous pathological conditions including metastatic tumors, neurodegenerative diseases and osteoarthritis.

Numerous MMP inhibitors are known in the art including small peptide inhibitors such as hydroxomate, non-microbial tetracyclins and monoclonal antibodies. While the former are limited by the high cost of production, high degradability, low oral bioavailability and lack of specificity, none of the latter have demonstrated in-vivo therapeutic efficacy.

The present inventors have previously uncovered that antibodies which recognize both electronic and structural determinants of the catalytic site of metalloenzymes can be used as potent inhibitors thereof Using haptens mimic the metalbound catalytic site of metalloenzymes as immunogens enabled the generation of highly efficient therapeutic antibodies which can be used to treat clinical conditions characterized by elevated metalloprotein activity (see WO2004/087042 to the present inventors).

While reducing the present invention to practice, the present inventors designed a novel hapten compound which closely mimic the local structure and conformation of the reactive zinc site inMMPs. The compound [2-(2-minoethyl-carbomoyl)-ethoxymethyl]-tris-[2-(N-(3-imidazol-1-yl-propyl)) ethoxymethyl]methane, termed, Imisdp (see FIG. 1), can mimic a 4-coordination geometry and similar force field induced by the zinc ion on coordinated three histidine array and water. A nearly tetrahedral conformation is formed by three imidazole bases and water molecule as the fourth ligand. FIG. 2A shows an overlay of the constructed 3D model of the Imisdp compound with the catalytic site of MMP-9 (PDB 1GKC) that has been modified to represent the tetrahedral geometry of the zinc ligands. The modifications include replacing the ligand present in the X-ray structure (an hydroxamate inhibitor) with a water molecule and optimization of the full enzyme to a local minimum by a multilayer QM/MM approach (see materials and methods). High similarity exists between the calculated histidine zinc motif in MMP-9 and Imisdp in terms of distances of the Histidines' ∈-nitrogen from the zinc ion (2.04±0.06 and 2.02 respectively) and the relative orientation of the three histidines toward the metal.

As is illustrated hereinbelow and in the Examples section which follows, the present inventors have immunized mice with Imisdp and screened for an MMP antibody cross-reactive with MMP-2 amd MMP-9. That antibody was termed 6C6 (See FIG. 10 and Examples 1-2 of the Examples section which follows). 6C6 was found to bind MMP-2/9 and competitively inhibit the activity of MMP-9, MMP-2 (Ki range 1

μM-5 μM) and MT1-MMP (Ki of 15 μM, see Table 4 below).The binding and inhibition of MMP-9 and MMP-2 was demonstrated in-vitro and in-situ by variety of biochemical and biophysical tools (see Examples 4-7 and 9). Importantly, 6C6 binds only the activated form of MMP-9 and MMP-2 (see Example 3 and Example 8). This enzyme form is lacking the pro-domain which shields the catalytic zinc complex residing within the enzyme moiety. The present inventors showed that antibodies generated according to the present method are capable of binding in vivo to MMP-9 (FIG. 11A). Furthermore, the present inventors showed that the antibodies of the present invention comprised therapeutic potential for the treatment of inflammatory bowel disease (Example 10).

Altogether, the present findings support the use of Imisdp as an important reagent (platform) for the production of metalloprotein inhibitors, and 6C6 and derived peptides and peptidomimetics as a valuable therapeutic tool.

These results demonstrates the potential in using these antibodies as a platform for the design of selective peptide inhibitors for individual MMPs by means of phage display and point mutations of the mAbs or their fragments.

Thus, according to one aspect of the present invention there is provided a compound having the general Formula (I):

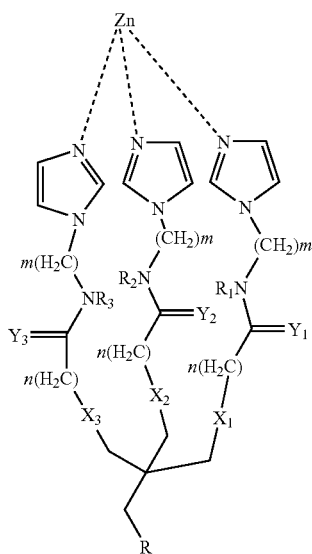

wherein:

m and n are each independently an integer from 1 to 6;

$X_1$-$X_3$ and $Y_1$-$Y_3$ are each independently O or S;

$R_1$-$R_3$ are each indepdnently selected from the group consisting of hydrogen, alkyl, and cycloalkyl; and R is $(CH_2)$x-C(=O)NR'—$(CH_2)$y-NR'R"

whereas:

x and y are each independently an integer from 1 to 6; and

R' and R" are each independently selected from the group consisting of hydrogen, alkyl, and cycloalkyl.

According to a preferred embodiment of this aspect of the present invention the compound is [2-(2-minoethylcarbomoyl)-ethoxymethyl]-tris[2-(N-(3-imidazol-1-yl-propyl))-ethoxymethyl]methane, termed, Imisdp, having the general Formula (II):

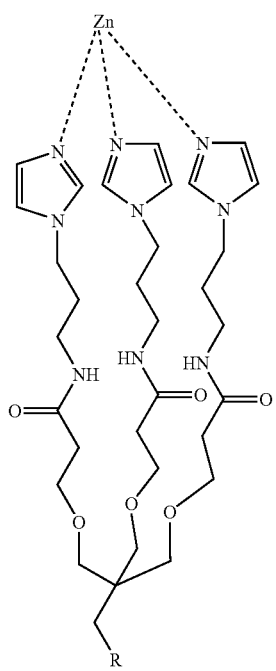

wherein R=—$CH_2$—C(=O)NH—$CH_2$—$CH_2$—$NH_2$

Synthesis of Imisdp is described in Example 7 of the Examples section which follows.

Since Imisdp mimics the local structure and transient conformation of the reactive zinc site in MMP-9 and MMP-2 it can be used for the production of metalloprotein inhibitors.

Thus, according to one aspect of the present invention, there is provided a method of producing a metalloprotein inhibitor.

The method is effected by generating antibodies or antibody fragments directed at the above-described compound (i.e., Imisdp). See Examples 1-2 as well as the "Materials and Methods" section of the Examples section which follows.

The "metalloprotein" of the present invention refers to a metal-bound protein, in which the metal binding site forms a part of an ezyme's catalytic domain, which both electronically and structurally resembles that of Imisdp.

The metalloprotein of this aspect of the present invention is preferably a metalloprotease—MMP (e.g., gelatinase such as MMP-2 and MMP-9).

It will be appreciated that all members of the MMP family are translated as latent enzymes, which upon activation are converted into active enzymes in which the metal ion in the active site is accessible for substrate binding. For example, the "cysteine switch model" has been previously suggested to explain MMP in vitro activation. The cysteine switch model suggests that upon activation, the latent zinc-binding site is converted to a catalytic zinc-binding site by dissociation of the thiol (Cys)-bearing propeptide from the zinc atom. Cleavage of the propeptide results in a breakdown of the pro-domain structure of the enzyme, and the shielding of the catalytic zinc ion is withdrawn. Consequently, the metal ion and the active site pocket are accessible for substrate binding and hydrolysis [Van Wart and Birkedal-Hansen (1990) Proc. Natl. Acad. Sci. USA 87, 5578-5582].

Antibodies and antibody fragments generated according to the teachings of the present invention serve as potent inhibitors of MMPs, due to their ability to bind both the metal ion and the coordinating amino acids within the catalytic zinc site, thereby specifically inhibiting the active conformation of these enzymes which are directly involved in pathological processes as described above.

As used herein the term "antibody", refers to an intact antibody molecule and the phrase "antibody fragment" refers to a functional fragment thereof, such as Fab, F(ab')$_2$, and Fv that are capable of binding to macrophages. These functional antibody fragments are defined as follows: (i) Fab, the fragment which contains a monovalent antigen-binding fragment of an antibody molecule, can be produced by digestion of whole antibody with the enzyme papain to yield an intact light chain and a portion of one heavy chain; (ii) Fab', the fragment of an antibody molecule that can be obtained by treating whole antibody with pepsin, followed by reduction, to yield an intact light chain and a portion of the heavy chain; two Fab' fragments are obtained per antibody molecule; (iii) (Fab')$_2$, the fragment of the antibody that can be obtained by treating whole antibody with the enzyme pepsin without subsequent reduction; F(ab')$_2$ is a dimer of two Fab' fragments held together by two disulfide bonds; (iv) Fv, defined as a genetically engineered fragment containing the variable region of the light chain and the variable region of the heavy chain expressed as two chains; (v) Single chain antibody ("SCA"), a genetically engineered molecule containing the variable region of the light chain and the variable region of the heavy chain, linked by a suitable polypeptide linker as a genetically fused single chain molecule; and (vi) Peptides coding for a single complementarity-determining region (CDR).

Methods of generating antibodies (i.e., monoclonal and polyclonal) are well known in the art. Antibodies may be generated via any one of several methods known in the art, which methods can employ induction of in vivo production of antibody molecules, screening immunoglobulin libraries or panels of highly specific binding reagents as disclosed [Orlandi D. R. et al. (1989) Proc. Natl. Acad. Sci. 86:3833-3837, Winter G. et al. (1991) Nature 349:293-299] or generation of monoclonal antibody molecules by continuous cell lines in culture. These include but are not limited to, the hybridoma technique, the human B-cell hybridoma technique, and the Epstein-Bar-Virus (EBV)-hybridoma technique [Kohler G., et al. (1975) Nature 256:495-497, Kozbor D., et al. (1985) J. Immunol. Methods 81:31-42, Cote R. J. et al. (1983) Proc. Natl. Acad. Sci. 80:2026-2030, Cole S. P. et al. (1984) Mol. Cell. Biol. 62:109-120].

In cases where the invention compounds are too small to elicit a strong immunogenic response, such antigens (haptens) can be coupled to antigenically neutral carriers such as keyhole limpet hemocyanin (KLH) or serum albumin [e.g., bovine serum albumine (BSA)] carriers (see U.S. Pat. Nos. 5,189,178 and 5,239,078 and Examples 2 of the Examples section). Coupling to carrier can be effected using methods well known in the art; For example, direct coupling to amino groups can be effected and optionally followed by reduction of imino linkage formed. Alternatively, the carrier can be coupled using condensing agents such as dicyclohexyl carbodiimide or other carbodiimide dehydrating agents. Linker compounds can also be used to effect the coupling; both homobifunctional and heterobifunctional linkers are available from Pierce Chemical Company, Rockford, Ill. The resulting immunogenic complex can then be injected into suitable mammalian subjects such as mice, rabbits, and the like. Suitable protocols involve repeated injection of the immunogen in the presence of adjuvants according to a schedule which boosts production of antibodies in the serum. The titers of the immune serum can readily be measured using immunoassay procedures which are well known in the art.

The antisera obtained can be used directly or monoclonal antibodies may be obtained as described hereinabove.

Antibody fragments can be obtained using methods well known in the art. (See for example, Harlow and Lane, Antibodies: A Laboratory Manual, Cold Spring Harbor Laboratory, New York, 1988, incorporated herein by reference). For example, antibody fragments according to the present invention can be prepared by proteolytic hydrolysis of the antibody or by expression in E. coli or mammalian cells (e.g. Chinese hamster ovary cell culture or other protein expression systems) of DNA encoding the fragment.

Alternatively, antibody fragments can be obtained by pepsin or papain digestion of whole antibodies by conventional methods. For example, antibody fragments can be produced by enzymatic cleavage of antibodies with pepsin to provide a 5S fragment denoted F(ab')$_2$. This fragment can be further cleaved using a thiol reducing agent, and optionally a blocking group for the sulfhydryl groups resulting from cleavage of disulfide linkages, to produce 3.5S Fab' monovalent fragments. Alternatively, an enzymatic cleavage using pepsin produces two monovalent Fab' fragments and an Fc fragment directly. These methods are described, for example, by Goldenberg, U.S. Pat. Nos. 4,036,945 and 4,331,647, and references contained therein, which patents are hereby incorporated by reference in their entirety. See also Porter, R. R., Biochem. J., 73: 119-126, 1959. Other methods of cleaving antibodies, such as separation of heavy chains to form monovalent light-heavy chain fragments, further cleavage of fragments, or other enzymatic, chemical, or genetic techniques may also be used, so long as the fragments bind to the antigen that is recognized by the intact antibody.

Fv fragments comprise an association of $V_H$ and $V_L$ chains. This association may be noncovalent, as described in Inbar et al., Proc. Nat'l Acad. Sci. USA 69:2659-62, 1972. Alternatively, the variable chains can be linked by an intermolecular disulfide bond or cross-linked by chemicals such as glutaraldehyde. Preferably, the Fv fragments comprise $V_H$ and $V_L$ chains connected by a peptide linker. These single-chain antigen binding proteins (sFv) are prepared by constructing a structural gene comprising DNA sequences encoding the $V_H$ and $V_L$ domains connected by an oligonucleotide. The structural gene is inserted into an expression vector, which is subsequently introduced into a host cell such as E. coli. The recombinant host cells synthesize a single polypeptide chain with a linker peptide bridging the two V domains. Methods for producing sFvs are described, for example, by Whitlow and Filpula, Methods, 2: 97-105, 1991; Bird et al., Science 242:423-426, 1988; Pack et al., Bio/Technology 11:1271-77, 1993; and Ladner et al., U.S. Pat. No. 4,946,778.

CDR peptides ("minimal recognition units") can be obtained by constructing genes encoding the CDR of an antibody of interest. Such genes are prepared, for example, by using the polymerase chain reaction to synthesize the variable region from RNA of antibody-producing cells. See, for example, Larrick and Fry, Methods, 2: 106-10, 1991.

It will be appreciated that for human therapy or diagnostics, humanized antibodies are preferably used. Humanized forms of non-human (e.g., murine) antibodies are chimeric molecules of immunoglobulins, immunoglobulin chains or fragments thereof (such as Fv, Fab, Fab', F(ab')$_2$ or other antigen-binding subsequences of antibodies) which contain minimal sequence derived from non-human immunoglobulin. Humanized antibodies include human immunoglobulins (recipient antibody) in which residues form a complementary determining region (CDR) of the recipient are replaced by residues from a CDR of a non-human species (donor antibody) such as mouse, rat or rabbit having the desired specificity, affinity and capacity. In some instances, Fv framework residues of the human immunoglobulin are replaced by corresponding non-human residues. Humanized antibodies may also comprise residues which are found neither in the recipient antibody nor in the imported CDR or framework sequences. In general, the humanized antibody will comprise substantially all of at least one, and typically two, variable domains, in which all or substantially all of the CDR regions correspond to those of a non-human immunoglobulin and all or substantially all of the FR regions are those of a human immunoglobulin consensus sequence. The humanized antibody optimally also will include at least a portion of an immunoglobulin constant region (Fc), typically that of a human immunoglobulin [Jones et al., Nature, 321:522-525 (1986); Riechmann et al., Nature, 332:323-329 (1988); and Presta, Curr. Op. Struct. Biol., 2:593-596 (1992)].

Methods for humanizing non-human antibodies are well known in the art. Generally, a humanized antibody has one or more amino acid residues introduced into it from a source which is non-human. These non-human amino acid residues are often referred to as import residues, which are typically taken from an import variable domain. Humanization can be essentially performed following the method of Winter and co-workers [Jones et al., Nature, 321:522-525 (1986); Riechmann et al., Nature 332:323-327 (1988); Verhoeyen et al., Science, 239:1534-1536 (1988)], by substituting rodent CDRs or CDR sequences for the corresponding sequences of a human antibody. Accordingly, such humanized antibodies are chimeric antibodies (U.S. Pat. No. 4,816,567), wherein substantially less than an intact human variable domain has been substituted by the corresponding sequence from a non-human species. In practice, humanized antibodies are typically human antibodies in which some CDR residues and possibly some FR residues are substituted by residues from analogous sites in rodent antibodies.

Human antibodies can also be produced using various techniques known in the art, including phage display libraries [Hoogenboom and Winter, J. Mol. Biol., 227:381 (1991); Marks et al., J. Mol. Biol., 222:581 (1991)]. The techniques of Cole et al. and Boemer et al. are also available for the preparation of human monoclonal antibodies (Cole et al., Monoclonal Antibodies and Cancer Therapy, Alan R. Liss, p. 77 (1985) and Boerner et al., J. Immunol., 147(1):86-95 (1991)]. Similarly, human can be made by introducing of human immunoglobulin loci into transgenic animals, e.g., mice in which the endogenous immunoglobulin genes have been partially or completely inactivated. Upon challenge, human antibody production is observed, which closely resembles that seen in humans in all respects, including gene rearrangement, assembly, and antibody repertoire. This approach is described, for example, in U.S. Pat. Nos. 5,545,807; 5,545, 806; 5,569,825; 5,625,126; 5,633,425; 5,661,016, and in the following scientific publications: Marks et al., Bio/Technology 10, 779-783 (1992); Lonberg et al., Nature 368 856-859 (1994); Morrison, Nature 368 812-13 (1994); Fishwild et al., Nature Biotechnology 14, 845-51 (1996); Neuberger, Nature Biotechnology 14, 826 (1996); Lonberg and Huszar, Intern. Rev. Immunol. 13 65-93 (1995).

Once antibodies are obtained, they may be tested for metalloprotein inhibitory activity. Appropriate assay conditions for metalloprotein inhibition activity are described in Knight et al., FEBS Letters 296(3):263-266(1992), Cawston et al., Anal. Biochem, 99:340-345 (1979), Cawston et al., Methods in Enzymology 80:771 et seq. (1981); Cawston et al., Biochem. J., 195:159-165 (1981), Weingarten et al., Biochem. Biophys. Res. Comm., 139:1184-1187 (1984) and U.S. Pat. Nos. 4,743,587 and 5,240,958.

As mentioned, using the above-methodology, the present inventors were able to produce a matrix metalloprotease (MMP) inhibitory antibody for MMP-2 and MMP-9, termed 6C6, a sequence of which is provided in SEQ ID NO: 1. CDR sequences are provided in SEQ ID NOs.7, 8, 9, 10, 11 and 12.

Thus, the present invention provides for any (poly)peptide sequence which comprises at least one of the above-mentioned CDR sequences as well as homologs and fragments thereof as long as its metalloprotein inhibitory activity is retained (specific inhibition of the catalytic activity of the metalloprotein). An example of such a polypeptide is an antibody (see above).

The term "polypeptide" as used herein encompasses native peptides (either degradation products, synthetically synthesized peptides or recombinant peptides) and peptidomimetics (typically, synthetically synthesized peptides), as well as peptoids and semipeptoids which are peptide analogs, which may have, for example, modifications rendering the peptides more stable while in a body or more capable of penetrating into cells. Such modifications include, but are not limited to N terminus modification, C terminus modification, peptide bond modification, including, but not limited to, $CH_2$—NH, $CH_2$—S, $CH_2$—S=O, O=C—NH, $CH_2$—O, $CH_2$—$CH_2$, S=C—NH, CH=CH or CF=CH, backbone modifications, and residue modification. Methods for preparing peptidomimetic compounds are well known in the art and are specified, for example, in Quantitative Drug Design, C.A. Ramsden Gd., Chapter 17.2, F. Choplin Pergamon Press (1992), which is incorporated by reference as if fully set forth herein. Further details in this respect are provided hereinunder.

Peptide bonds (—CO—NH—) within the peptide may be substituted, for example, by N-methylated bonds (—N($CH_3$)—CO—), ester bonds (—C(R)H—C—O—O—C(R)—N—), ketomethylen bonds (—CO—$CH_2$—), α-aza bonds (—NH—N(R)—CO—), wherein R is any alkyl, e.g., methyl, carba bonds (—$CH_2$—NH—), hydroxyethylene bonds (—CH(OH)—$CH_2$—), thioamide bonds (—CS—NH—), olefinic double bonds (—CH=CH—), retro amide bonds (—NH—CO—), peptide derivatives (—N(R)—$CH_2$—CO—), wherein R is the "normal" side chain, naturally presented on the carbon atom.

These modifications can occur at any of the bonds along the peptide chain and even at several (2-3) at the same time.

Natural aromatic amino acids, Trp, Tyr and Phe, may be substituted for synthetic non-natural acid such as Phenylglycine, Tic, naphtylalanine (Nal), phenylisoserine, threoninol, ring-methylated derivatives of Phe, halogenated derivatives of Phe or o-methyl-Tyr.

In addition to the above, the peptides of the present invention may also include one or more modified amino acids or one or more non-amino acid monomers (e.g. fatty acids, complex carbohydrates etc).

As used herein in the specification and in the claims section below the term "amino acid" or "amino acids" is understood to include the 20 naturally occurring amino acids; those amino acids often modified post-translationally in vivo, including, for example, hydroxyproline, phosphoserine and phosphothreonine; and other unusual amino acids including, but not limited to, 2-aminoadipic acid, hydroxylysine, isodesmosine, nor-valine, nor-leucine and ornithine. Furthermore, the term "amino acid" includes both D- and L-amino acids.

Tables 1 and 2 below list naturally occurring amino acids (Table 1) and non-conventional or modified amino acids (e.g., synthetic, Table 2) which can be used with the present invention.

TABLE 1

| Amino Acid | Three-Letter Abbreviation | One-letter Symbol |
|---|---|---|
| alanine | Ala | A |
| Arginine | Arg | R |
| Asparagine | Asn | N |
| Aspartic acid | Asp | D |
| Cysteine | Cys | C |
| Glutamine | Gln | Q |
| Glutamic Acid | Glu | E |
| glycine | Gly | G |
| Histidine | His | H |
| isoleucine | Iie | I |
| leucine | Leu | L |
| Lysine | Lys | K |
| Methionine | Met | M |
| phenylalanine | Phe | F |
| Proline | Pro | P |
| Serine | Ser | S |
| Threonine | Thr | T |
| tryptophan | Trp | W |
| tyrosine | Tyr | Y |
| Valine | Val | V |
| Any amino acid as above | Xaa | X |

TABLE 2

| Non-conventional amino acid | Code | Non-conventional amino acid | Code |
|---|---|---|---|
| α-aminobutyric acid | Abu | L-N-methylalanine | Nmala |
| α-amino-α-methylbutyrate | Mgabu | L-N-methylarginine | Nmarg |
| aminocyclopropane-carboxylate | Cpro | L-N-methylasparagine | Nmasn |
|  |  | L-N-methylaspartic acid | Nmasp |
| aminoisobutyric acid | Aib | L-N-methylcysteine | Nmcys |
| aminonorbornyl-carboxylate | Norb | L-N-methylglutamine | Nmgln |
|  |  | L-N-methylglutamic acid | Nmglu |
| cyclohexylalanine | Chexa | L-N-methylhistidine | Nmhis |
| cyclopentylalanine | Cpen | L-N-methylisolleucine | Nmile |
| D-alanine | Dal | L-N-methylleucine | Nmleu |
| D-arginine | Darg | L-N-methyllysine | Nmlys |
| D-aspartic acid | Dasp | L-N-methylmethionine | Nmmet |
| D-cysteine | Dcys | L-N-methylnorleucine | Nmnle |
| D-glutamine | Dgln | L-N-methylnorvaline | Nmnva |
| D-glutamic acid | Dglu | L-N-methylornithine | Nmorn |
| D-histidine | Dhis | L-N-methylphenylalanine | Nmphe |
| D-isoleucine | Dile | L-N-methylproline | Nmpro |
| D-leucine | Dleu | L-N-methylserine | Nmser |
| D-lysine | Dlys | L-N-methylthreonine | Nmthr |
| D-methionine | Dmet | L-N-methyltryptophan | Nmtrp |
| D-ornithine | Dorn | L-N-methyltyrosine | Nmtyr |
| D-phenylalanine | Dphe | L-N-methylvaline | Nmval |
| D-proline | Dpro | L-N-methylethylglycine | Nmetg |
| D-serine | Dser | L-N-methyl-t-butylglycine | Nmtbug |
| D-threonine | Dthr | L-norleucine | Nle |
| D-tryptophan | Dtrp | L-norvaline | Nva |
| D-tyrosine | Dtyr | α-methyl-aminoisobutyrate | Maib |
| D-valine | Dval | α-methyl-γ-aminobutyrate | Mgabu |
| D-α-methylalanine | Dmala | α-methylcyclohexylalanine | Mchexa |
| D-α-methylarginine | Dmarg | α-methylcyclopentylalanine | Mcpen |
| D-α-methylasparagine | Dmasn | α-methyl-α-napthylalanine | Manap |
| D-α-methylaspartate | Dmasp | α-methylpenicillamine | Mpen |
| D-α-methylcysteine | Dmcys | N-(4-aminobutyl)glycine | Nglu |
| D-α-methylglutamine | Dmgln | N-(2-aminoethyl)glycine | Naeg |
| D-α-methylhistidine | Dmhis | N-(3-aminopropyl)glycine | Norn |
| D-α-methylisoleucine | Dmile | N-amino-α-methylbutyrate | Nmaabu |
| D-α-methylleucine | Dmleu | α-napthylalanine | Anap |
| D-α-methyllysine | Dmlys | N-benzylglycine | Nphe |
| D-α-methylmethionine | Dmmet | N-(2-carbamylethyl)glycine | Ngln |
| D-α-methylornithine | Dmorn | N-(carbamylmethyl)glycine | Nasn |
| D-α-methylphenylalanine | Dmphe | N-(2-carboxyethyl)glycine | Nglu |
| D-α-methylproline | Dmpro | N-(carboxymethyl)glycine | Nasp |
| D-α-methylserine | Dmser | N-cyclobutylglycine | Ncbut |
| D-α-methylthreonine | Dmthr | N-cycloheptylglycine | Nchep |
| D-α-methyltryptophan | Dmtrp | N-cyclohexylglycine | Nchex |
| D-α-methyltyrosine | Dmty | N-cyclodecylglycine | Ncdec |
| D-α-methylvaline | Dmval | N-cyclododeclglycine | Ncdod |
| D-α-methylalnine | Dnmala | N-cyclooctylglycine | Ncoct |
| D-α-methylarginine | Dnmarg | N-cyclopropylglycine | Ncpro |
| D-α-methylasparagine | Dnmasn | N-cycloundecylglycine | Ncund |
| D-α-methylasparatate | Dnmasp | N-(2,2-diphenylethyl)glycine | Nbhm |
| D-α-methylcysteine | Dnmcys | N-(3,3-diphenylpropyl)glycine | Nbhe |
| D-N-methylleucine | Dnmleu | N-(3-indolylethyl) glycine | Nhtrp |
| D-N-methyllysine | Dnmlys | N-methyl-γ-aminobutyrate | Nmgabu |
| N-methylcyclohexylalanine | Nmchexa | D-N-methylmethionine | Dnmmet |
| D-N-methylornithine | Dnmorn | N-methylcyclopentylalanine | Nmcpen |
| N-methylglycine | Nala | D-N-methylphenylalanine | Dnmphe |
| N-methylaminoisobutyrate | Nmaib | D-N-methylproline | Dnmpro |
| N-(1-methylpropyl)glycine | Nile | D-N-methylserine | Dnmser |

TABLE 2-continued

| Non-conventional amino acid | Code | Non-conventional amino acid | Code |
|---|---|---|---|
| N-(2-methylpropyl)glycine | Nile | D-N-methylserine | Dnmser |
| N-(2-methylpropyl)glycine | Nleu | D-N-methylthreonine | Dnmthr |
| D-N-methyltryptophan | Dnmtrp | N-(1-methylethyl)glycine | Nva |
| D-N-methyltyrosine | Dnmtyr | N-methyla-napthylalanine | Nmanap |
| D-N-methylvaline | Dnmval | N-methylpenicillamine | Nmpen |
| γ-aminobutyric acid | Gabu | N-(p-hydroxyphenyl)glycine | Nhtyr |
| L-t-butylglycine | Tbug | N-(thiomethyl)glycine | Ncys |
| L-ethylglycine | Etg | penicillamine | Pen |
| L-homophenylalanine | Hphe | L-α-methylalanine | Mala |
| L-α-methylarginine | Marg | L-α-methylasparagine | Masn |
| L-α-methylaspartate | Masp | L-α-methyl-t-butylglycine | Mtbug |
| L-α-methylcysteine | Mcys | L-methylethylglycine | Metg |
| L-α-methylglutamine | Mgln | L-α-methylglutamate | Mglu |
| L-α-methylhistidine | Mhis | L-α-methylhomo phenylalanine | Mhphe |
| L-α-methylisoleucine | Mile | N-(2-methylthioethyl)glycine | Nmet |
| D-N-methylglutamine | Dnmgln | N-(3-guanidinopropyl)glycine | Narg |
| D-N-methylglutamate | Dnmglu | N-(1-hydroxyethyl)glycine | Nthr |
| D-N-methylhistidine | Dnmhis | N-(hydroxyethyl)glycine | Nser |
| D-N-methylisoleucine | Dnmile | N-(imidazolylethyl)glycine | Nhis |
| D-N-methylleucine | Dnmleu | N-(3-indolylyethyl)glycine | Nhtrp |
| D-N-methyllysine | Dnmlys | N-methyl-γ-aminobutyrate | Nmgabu |
| N-methylcyclohexylalanine | Nmchexa | D-N-methylmethionine | Dnmmet |
| D-N-methylornithine | Dnmorn | N-methylcyclopentylalanine | Nmcpen |
| N-methylglycine | Nala | D-N-methylphenylalanine | Dnmphe |
| N-methylaminoisobutyrate | Nmaib | D-N-methylproline | Dnmpro |
| N-(1-methylpropyl)glycine | Nile | D-N-methylserine | Dnmser |
| N-(2-methylpropyl)glycine | Nleu | D-N-methylthreonine | Dnmthr |
| D-N-methyltryptophan | Dnmtrp | N-(1-methylethyl)glycine | Nval |
| D-N-methyltyrosine | Dnmtyr | N-methyla-napthylalanine | Nmanap |
| D-N-methylvaline | Dnmval | N-methylpenicillamine | Nmpen |
| γ-aminobutyric acid | Gabu | N-(p-hydroxyphenyl)glycine | Nhtyr |
| L-t-butylglycine | Tbug | N-(thiomethyl)glycine | Ncys |
| L-ethylglycine | Etg | penicillamine | Pen |
| L-homophenylalanine | Hphe | L-α-methylalanine | Mala |
| L-α-methylarginine | Marg | L-α-methylasparagine | Masn |
| L-α-methylaspartate | Masp | L-α-methyl-t-butylglycine | Mtbug |
| L-α-methylcysteine | Mcys | L-methylethylglycine | Metg |
| L-α-methylglutamine | Mgln | L-α-methylglutamate | Mglu |
| L-α-methylhistidine | Mhis | L-α-methylhomophenylalanine | Mhphe |
| L-α-methylisoleucine | Mile | N-(2-methylthioethyl)glycine | Nmet |
| L-α-methylleucine | Mleu | L-α-methyllysine | Mlys |
| L-α-methylmethionine | Mmet | L-α-methylnorleucine | Mnle |
| L-α-methylnorvaline | Mnva | L-α-methylornithine | Morn |
| L-α-methylphenylalanine | Mphe | L-α-methylproline | Mpro |
| L-α-methylserine | mser | L-α-methylthreonine | Mthr |
| L-α-methylvaline | Mtrp | L-α-methyltyrosine | Mtyr |
| L-α-methylleucine | Mval Nnbhm | L-N-methylhomophenylalanine | Nmhphe |
| N-(N-(2,2-diphenylethyl) carbamylmethyl-glycine | Nnbhm | N-(N-(3,3-diphenylpropyl) carbamylmethyl(1)glycine | Nnbhe |
| 1-carboxy-1-(2,2-diphenyl ethylamino)cyclopropane | Nmbc | | |

Peptides with improved affinity to a metalloprotease of interest or enhanced biological activity may be generated by methods well known in the art including phage display and computational biology.

The peptides of the present invention may be synthesized by any techniques that are known to those skilled in the art of peptide synthesis. For solid phase peptide synthesis, a summary of the many techniques may be found in: Stewart, J. M. and Young, J. D. (1963), "Solid Phase Peptide Synthesis," W. H. Freeman Co. (San Francisco); and Meienhofer, J (1973). "Hormonal Proteins and Peptides," vol. 2, p. 46, Academic Press (New York). For a review of classical solution synthesis, see Schroder, G. and Lupke, K. (1965). The Peptides, vol. 1, Academic Press (New York). For recombinant techniques see references further below.

Also contemplates are nucleic acid sequences which encode the above-described polypeptide sequences (see SEQ ID NOs. 13, 14, 15, 16, 17 and 18).

As is mentioned hereinabove, one specific use for the antibodies of the present invention is prevention or treatment of diseases associated with imbalanced or abnormal activity of metalloproteins such as metalloproteases.

Examples of such disease include, but are not limited to, arthritic diseases, such as osteoarthritis (OA), rheumatoid arthritis (RA), septic arthritis, soft tissue rheumatism, polychondritis and tendonitis; metastatic tumors, periodontal diseases; corneal ulceration, such as induced by alkali or other burns, by radiation, by vitamin E or retinoid deficiency; glomerular diseases, such as proteinuria, dytrophobic epidermolysis bullosa; bone resorption diseases, such as osteoporosis, Paget's disease, hyperparathyroidism and cholesteatoma; birth control through preventing ovulation or implantation; angiogenesis relating to tumor growth or to the neovascularization associated with diabetic retinopathy and macular degeneration; coronary thrombosis associated with atherosclerotic plaque rupture; pulmonary emphysema, wound healing and HIV infection.

As illustrated in Example 10, the present inventors have shown that the antibodies of the present invention may be used to treat an irritable bowel disease.

Inflammatory bowel diseases (IBD) are severe gastrointestinal disorders characterized by intestinal inflammation and tissue remodeling, that increase in frequency and may prove disabling for patients. The major forms of IBD, ulcerative colitis (UC) and Crohn's disease are chronic, relapsing conditions that are clinically characterized by abdominal pain, diarrhea, rectal bleeding, and fever.

Thus, according to another aspect of the present invention there is provided a method of inhibiting matrix metalloprotease activity in a subject in need thereof.

Preferred individual subjects according to the present invention are animals such as mammals (e.g., canines, felines, ovines, porcines, equines, bovines, primates) preferably, humans.

The method comprises providing to the subject a therapeutically effective amount of the MMP inhibitor of the present invention (i.e., the antibody or antibody fragments, described hereinabove).

As is further detailed hereinbelow, the MMP inhibitor can be provided via direct administration (e.g., oral administration or injection) or it can be expressed from a polynucleotide construct administered to target cells of the individual.

The MMP inhibitors of the present invention can be provided to an individual per se, or as part of a pharmaceutical composition where it is mixed with a pharmaceutically acceptable carrier.

As used herein a "pharmaceutical composition" refers to a preparation of one or more of the active ingredients described herein with other chemical components such as physiologically suitable carriers and excipients. The purpose of a pharmaceutical composition is to facilitate administration of a compound to an organism.

Herein the term "active ingredient" refers to the antibody preparation, which is accountable for the biological effect.

Hereinafter, the phrases "physiologically acceptable carrier" and "pharmaceutically acceptable carrier" which may be interchangeably used refer to a carrier or a diluent that does not cause significant irritation to an organism and does not abrogate the biological activity and properties of the administered compound. An adjuvant is included under these phrases. One of the ingredients included in the pharmaceutically acceptable carrier can be for example polyethylene glycol (PEG), a biocompatible polymer with a wide range of solubility in both organic and aqueous media (Mutter et al. (1979).

Herein the term "excipient" refers to an inert substance added to a pharmaceutical composition to further facilitate administration of an active ingredient. Examples, without limitation, of excipients include calcium carbonate, calcium phosphate, various sugars and types of starch, cellulose derivatives, gelatin, vegetable oils and polyethylene glycols.

Techniques for formulation and administration of drugs may be found in "Remington's Pharmaceutical Sciences," Mack Publishing Co., Easton, Pa., latest edition, which is incorporated herein by reference.

Suitable routes of administration may, for example, include oral, rectal, transmucosal, especially transnasal, intestinal or parenteral delivery, including intramuscular, subcutaneous and intramedullary injections as well as intrathecal, direct intraventricular, intravenous, inrtaperitoneal, intranasal, or intraocular injections.

Alternately, one may administer a preparation in a local rather than systemic manner, for example, via injection of the preparation directly into a specific region of a patient's body.

Pharmaceutical compositions of the present invention may be manufactured by processes well known in the art, e.g., by means of conventional mixing, dissolving, granulating, dragee-making, levigating, emulsifying, encapsulating, entrapping or lyophilizing processes.

Pharmaceutical compositions for use in accordance with the present invention may be formulated in conventional manner using one or more physiologically acceptable carriers comprising excipients and auxiliaries, which facilitate processing of the active ingredients into preparations which, can be used pharmaceutically. Proper formulation is dependent upon the route of administration chosen.

For injection, the active ingredients of the invention may be formulated in aqueous solutions, preferably in physiologically compatible buffers such as Hank's solution, Ringer's solution, or physiological salt buffer. For transmucosal administration, penetrants appropriate to the barrier to be permeated are used in the formulation. Such penetrants are generally known in the art.

For oral administration, the compounds can be formulated readily by combining the active compounds with pharmaceutically acceptable carriers well known in the art. Such carriers enable the compounds of the invention to be formulated as tablets, pills, dragees, capsules, liquids, gels, syrups, slurries, suspensions, and the like, for oral ingestion by a patient. Pharmacological preparations for oral use can be made using a solid excipient, optionally grinding the resulting mixture, and processing the mixture of granules, after adding suitable auxiliaries if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carbomethyl-cellulose; and/or physiologically acceptable polymers such as polyvinylpyrrolidone (PVP). If desired, disintegrating agents may be added, such as cross-linked polyvinyl pyrrolidone, agar, or alginic acid or a salt thereof such as sodium alginate.

Dragee cores are provided with suitable coatings. For this purpose, concentrated sugar solutions may be used which may optionally contain gum arabic, talc, polyvinyl pyrrolidone, carbopol gel, polyethylene glycol, titanium dioxide, lacquer solutions and suitable organic solvents or solvent mixtures. Dyestuffs or pigments may be added to the tablets or dragee coatings for identification or to characterize different combinations of active compound doses.

Pharmaceutical compositions, which can be used orally, include push-fit capsules made of gelatin as well as soft, sealed capsules made of gelatin and a plasticizer, such as glycerol or sorbitol. The push-fit capsules may contain the active ingredients in admixture with filler such as lactose, binders such as starches, lubricants such as talc or magnesium stearate and, optionally, stabilizers. In soft capsules, the active ingredients may be dissolved or suspended in suitable liquids, such as fatty oils, liquid paraffin, or liquid polyethylene glycols. In addition, stabilizers may be added. All formulations for oral administration should be in dosages suitable for the chosen route of administration.

For buccal administration, the compositions may take the form of tablets or lozenges formulated in conventional manner.

For administration by nasal inhalation, the active ingredients for use according to the present invention are conveniently delivered in the form of an aerosol spray presentation from a pressurized pack or a nebulizer with the use of a suitable propellant, e.g., dichlorodifluoromethane, trichlorofluoromethane, dichloro-tetrafluoroethane or carbon dioxide. In the case of a pressurized aerosol, the dosage unit may be determined by providing a valve to deliver a metered amount.

Capsules and cartridges of, e.g., gelatin for use in a dispenser may be formulated containing a powder mix of the compound and a suitable powder base such as lactose or starch.

The preparations described herein may be formulated for parenteral administration, e.g., by bolus injection or continuous infusion. Formulations for injection may be presented in unit dosage form, e.g., in ampoules or in multidose containers with optionally, an added preservative. The compositions may be suspensions, solutions or emulsions in oily or aqueous vehicles, and may contain formulatory agents such as suspending, stabilizing and/or dispersing agents.

Pharmaceutical compositions for parenteral administration include aqueous solutions of the active preparation in water-soluble form. Additionally, suspensions of the active ingredients may be prepared as appropriate oily or water based injection suspensions. Suitable lipophilic solvents or vehicles include fatty oils such as sesame oil, or synthetic fatty acids esters such as ethyl oleate, triglycerides or liposomes. Aqueous injection suspensions may contain substances, which increase the viscosity of the suspension, such as sodium carboxymethyl cellulose, sorbitol or dextran. Optionally, the suspension may also contain suitable stabilizers or agents which increase the solubility of the active ingredients to allow for the preparation of highly concentrated solutions.

Alternatively, the active ingredient may be in powder form for constitution with a suitable vehicle, e.g., sterile, pyrogen-free water based solution, before use.

The preparation of the present invention may also be formulated in rectal compositions such as suppositories or retention enemas, using, e.g., conventional suppository bases such as cocoa butter or other glycerides.

Pharmaceutical compositions suitable for use in context of the present invention include compositions wherein the active ingredients are contained in an amount effective to achieve the intended purpose. More specifically, a therapeutically effective amount means an amount of active ingredients effective to prevent, alleviate or ameliorate symptoms of disease or prolong the survival of the subject being treated.

Determination of a therapeutically effective amount is well within the capability of those skilled in the art.

For any preparation used in the methods of the invention, the therapeutically effective amount or dose can be estimated initially from in vitro assays. For example, a dose can be formulated in animal models and such information can be used to more accurately determine useful doses in humans.

Toxicity and therapeutic efficacy of the active ingredients described herein can be determined by standard pharmaceutical procedures in vitro, in cell cultures or experimental animals. The data obtained from these in vitro and cell culture assays and animal studies can be used in formulating a range of dosage for use in human. The dosage may vary depending upon the dosage form employed and the route of administration utilized. The exact formulation, route of administration and dosage can be chosen by the individual physician in view of the patient's condition. [See e.g., Fingl, et al., (1975) "The Pharmacological Basis of Therapeutics", Ch. 1 p.1].

Depending on the severity and responsiveness of the condition to be treated, dosing can be of a single or a plurality of administrations, with course of treatment lasting from several days to several weeks or until cure is effected or diminution of the disease state is achieved.

The amount of a composition to be administered will, of course, be dependent on the subject being treated, the severity of the affliction, the manner of administration, the judgment of the prescribing physician, etc.

Compositions including the preparation of the present invention formulated in a compatible pharmaceutical carrier may also be prepared, placed in an appropriate container, and labeled for treatment of an indicated condition.

Compositions of the present invention may, if desired, be presented in a pack or dispenser device, such as an FDA approved kit, which may contain one or more unit dosage forms containing the active ingredient. The pack may, for example, comprise metal or plastic foil, such as a blister pack. The pack or dispenser device may be accompanied by instructions for administration. The pack or dispenser may also be accommodated by a notice associated with the container in a form prescribed by a governmental agency regulating the manufacture, use or sale of pharmaceuticals, which notice is reflective of approval by the agency of the form of the compositions or human or veterinary administration. Such notice, for example, may be of labeling approved by the U.S. Food and Drug Administration for prescription drugs or of an approved product insert.

As described hereinabove, the antibody inhibitors of the present invention can be expressed from a nucleic acid construct.

It will be appreciated that polynucleotides encoding the antibodies of the present invention preferably further encode a signal peptide which allows secretion or trafficking of the antibodies into a subcellular or extracellular localization of interest. For example, when the target metalloprotein is an MMP, a secretory signal peptide is preferably conjugated inframe to the polynucleotide encoding antibody segment.

It will be further appreciated that recombinant single-chain Fv (ScFv) fragments may be preferably expressed because of their considerably less complicated structure as compared to whole antibody molecules. As described hereinabove ScFvs are proteins consisting of the $V_L$ and $V_H$ antibody polypeptide chains synthesized as a single chain with the carboxyl terminus of $V_L$ linked by a peptide bridge to the amino terminus of $V_H$ Methods for recombinantly producing these peptides are well known in the art [see Bird et al., Science 242:423-426 (1988); Huston et al., Proc. Nat'l Acad. Sci. USA 85:5879-5883 (1988); and de Kruif et al., J. Mol. Biol. 248:97-105 (1995)]. According to embodiments of this aspect of the present invention, following immunization with the compounds of the present invention, splenic, mRNA is harvested from the immunized animal and used to produce a cDNA library in a bacteriophage which displays the ScFv fragments. Phage particles are then screened to determine those that interact specifically and Preferably with the activated form of the metallop[rotein of interest. ScFv segments are recovered from these phage particles, and cloned into an expression construct (see U.S. Pat. No. 5,800,814).

The nucleic acid constructs of this aspect of the present invention can be administered to target cells of the individual subject (i.e., in-vivo gene therapy).

Alternatively, the nucleic acid construct is introduced into a suitable cell via an appropriate gene delivery vehicle/method (transfection, transduction, homologous recombination, etc.) and an expression system as needed and then the modified cells are expanded in culture and returned to the individual (i.e., ex-vivo gene therapy).

To enable cellular expression of the antibodies or antibody fragments of the present invention, the nucleic acid construct of the present invention further includes at least one cis acting regulatory element. As used herein, the phrase "cis acting regulatory element" refers to a polynucleotide sequence, preferably a promoter, which binds a trans acting regulator and regulates the transcription of a coding sequence located downstream thereto.

Any available promoter can be used by the present methodology. In a preferred embodiment of the present invention, the promoter utilized by the nucleic acid construct of the present invention is active in the specific cell population transformed. Examples of cell type-specific and/or tissue-specific promoters include promoters such as albumin that is liver specific [Pinkert et al., (1987) Genes Dev. 1:268-277], lymphoid specific promoters [Calame et al., (1988) Adv. Immunol. 43:235-275]; in particular promoters of T-cell receptors [Winoto et al., (1989) EMBO J. 8:729-733] and immunoglobulins; [Banerji et al. (1983) Cell 33729-740], neuron-specific promoters such as the neurofilament promoter [Byrne et al. (1989) Proc. Natl. Acad. Sci. USA 86:5473-5477], pancreas-specific promoters [Edlunch et al. (1985) Science 230:912-916] or mammary gland-specific promoters such as the milk whey promoter (U.S. Pat. No. 4,873,316 and European Application Publication No. 264, 166). The nucleic acid construct of the present invention can further include an enhancer, which can be adjacent or distant to the promoter sequence and can function in up regulating the transcription therefrom.

The constructs of the present methodology preferably further include an appropriate selectable marker and/or an origin of replication. Preferably, the construct utilized is a shuttle vector, which can propagate both in E. coli (wherein the construct comprises an appropriate selectable marker and origin of replication) and be compatible for propagation in cells, or integration in a gene and a tissue of choice. The construct according to the present invention can be, for example, a plasmid, a bacmid, a phagemid, a cosmid, a phage, a virus or an artificial chromosome.

Currently preferred in vivo nucleic acid transfer techniques include transfection with viral or non-viral constructs, such as adenovirus, lentivirus, Herpes simplex I virus, or adeno-associated virus (AAV) and lipid-based systems. Useful lipids for lipid-mediated transfer of the gene are, for example, DOTMA, DOPE, and DC-Chol [Tonkinson et al., Cancer Investigation, 14(1): 54-65 (1996)]. The most preferred constructs for use in gene therapy are viruses, most preferably adenoviruses, AAV, lentiviruses, or retroviruses. A viral construct such as a retroviral construct includes at least one transcriptional promoter/enhancer or locus-defining element(s), or other elements that control gene expression by other means such as alternate splicing, nuclear RNA export, or post-translational modification of messenger. Such vector constructs also include a packaging signal, long terminal repeats (LTRs) or portions thereof, and positive and negative strand primer binding sites appropriate to the virus used, unless it is already present in the viral construct. In addition, such a construct typically includes a signal sequence for secretion of the peptide or antibody from a host cell in which it is placed. Preferably the signal sequence for this purpose is a mammalian signal sequence. Optionally, the construct may also include a signal that directs polyadenylation, as well as one or more restriction sites and a translation termination sequence. By way of example, such constructs will typically include a 5' LTR, a tRNA binding site, a packaging signal, an origin of second-strand DNA synthesis, and a 3' LTR or a portion thereof. Other vectors can be used that are non-viral, such as cationic lipids, polylysine, and dendrimers.

Preferred modes for executing gene therapy protocols are provided in Somia and Verma [(2000) Nature Reviews 1:91-99], Isner (2002) Myocardial gene therapy. Nature 415:234-239; High (2001) Gene therapy: a 2001 perspective. Haemophilia 7:23-27; and Hammond and McKirnan (2001) Angiogenic gene therapy for heart disease: a review of animal studies and clinical trials. 49:561-567.

Because of the ability of the antibodies of the present invention to differentially recognize the activated form of metalloprotein (see Example 3 of the Examples section), they can be used as potent diagnostic and prognostic tools, such as by monitoring MMP activity in a biological sample [i.e., any body sample such as blood (serum or plasma), sputum, ascites fluids, pleural effusions, urine, biopsy specimens, isolated cells and/or cell membrane preparation]. This is of special significance when evaluating the metastatic features of cancer cells, wherein imbalanced activation of MMPs facilitate tumor invasion. Likewise, the antibodies of the present invention can be used in monitoring therapeutic dosage of MMP inhibitors. For such applications the antibodies of the present invention are preferably labeled with each of any radioactive, fluorescent, biological or enzymatic tags or labels of standard use in the art. U.S. Patents concerning the use of such labels include U.S. Pat. Nos. 3,817,837; 3,850,752; 3,939,350; 3,996,345; 4,277,437; 4,275,149 and 4,366,241.

It will be appreciated that such detection methods can also be used for high throughput screening of novel MMPs. Briefly, multiple biological samples can be contacted with the antibodies of the present invention, where activated MMPs can bind thereto. Measures are taken to use biological samples, which include activated MMPs such as those derived from tumor cell-lines. Typically, a radioactive label is used to reduce the assay volume.

Alternatively, the antibodies of the present invention can be used to purify active metalloenzymes from biological samples.

Numerous protein purification methods are known in the art. For example, the antibodies or antibody fragments of the present invention can be used in affinity chromatography for isolating the metalloenzymes. Columns can be prepared where the antibodies are linked to a solid substrate, e.g., particles, such as agarose, Sephadex, and the like, and the biological sample, such as a cell lysate may be passed through the column, the column washed, followed by increasing concentrations of a mild denaturant, whereby the purified metalloenzyme will be released.

The antibodies or fragments thereof generated according to the teachings of the present invention can be included in a diagnostic or therapeutic kit. Antibodies or antibody fragments can be packaged in a one or more containers with appropriate buffers and preservatives and used for diagnosis or for directing therapeutic treatment.

Thus, the antibodies or fragments thereof can be each mixed in a single container or placed in individual containers. Preferably, the containers include a label. Suitable containers include, for example, bottles, vials, syringes, and test tubes. The containers may be formed from a variety of materials such as glass or plastic.

In addition, other additives such as stabilizers, buffers, blockers and the like may also be added. The antibodies of such kits can also be attached to a solid support, such as beads, array substrate (e.g., chips) and the like and used for diagnostic purposes. The kit can also include instructions for determining if the tested subject is suffering from, or is at risk of developing, a condition, disorder, or disease associated with expression of an MMP of interest.

Additional objects, advantages, and novel features of the present invention will become apparent to one ordinarily skilled in the art upon examination of the following examples, which are not intended to be limiting. Additionally, each of the various embodiments and aspects of the present invention as delineated hereinabove and as claimed in the claims section below finds experimental support in the following examples.

EXAMPLES

Reference is now made to the following examples, which together with the above descriptions, illustrate the invention in a non limiting fashion.

Generally, the nomenclature used herein and the laboratory procedures utilized in the present invention include molecular, biochemical, microbiological and recombinant DNA techniques. Such techniques are thoroughly explained in the literature. See, for example, "Molecular Cloning: A laboratory Manual" Sambrook et al., (1989); "Current Protocols in Molecular Biology" Volumes I-III Ausubel, R. M., ed. (1994); Ausubel et al., "Current Protocols in Molecular Biology", John Wiley and Sons, Baltimore, Maryland (1989); Perbal, "A Practical Guide to Molecular Cloning", John Wiley & Sons, New York (1988); Watson et al., "Recombinant DNA", Scientific American Books, New York; Birren et al. (eds) "Genome Analysis: A Laboratory Manual Series", Vols. 1-4, Cold Spring Harbor Laboratory Press, New York (1998); methodologies as set forth in U.S. Pat. Nos. 4,666,828; 4,683,202; 4,801,531; 5,192,659 and 5,272,057; "Cell Biology: A Laboratory Handbook", Volumes I-III Cellis, J. E., ed. (1994); "Current Protocols in Immunology" Volumes I-III Coligan J. E., ed. (1994); Stites et al. (eds), "Basic and Clinical Immunology" (8th Edition), Appleton & Lange, Norwalk, CT (1994); Mishell and Shiigi (eds), "Selected Methods in Cellular Immunology", W. H. Freeman and Co., New York (1980); available immunoassays are extensively described in the patent and scientific literature, see, for example, U.S. Pat. Nos. 3,791,932; 3,839,153; 3,850,752; 3,850,578; 3,853,987; 3,867,517; 3,879,262; 3,901,654; 3,935,074; 3,984,533; 3,996,345; 4,034,074; 4,098,876; 4,879,219; 5,011,771 and 5,281,521; "Oligonucleotide Synthesis" Gait, M. J., ed. (1984); "Nucleic Acid Hybridization" Hames, B. D., and Higgins S. J., eds. (1985); "Transcription and Translation" Hames, B. D., and Higgins S. J., Eds. (1984); "Animal Cell Culture" Freshney, R. I., ed. (1986); "Immobilized Cells and Enzymes" IRL Press, (1986); "A Practical Guide to Molecular Cloning" Perbal, B., (1984) and "Methods in Enzymology" Vol. 1-317, Academic Press; "PCR Protocols: A Guide To Methods And Applications", Academic Press, San Diego, Calif. (1990); Marshak et al., "Strategies for Protein Purification and Characterization—A Laboratory Course Manual" CSHL Press (1996); all of which are incorporated by reference as if fully set forth herein. Other general references are provided throughout this document. The procedures therein are believed to be well known in the art and are provided for the convenience of the reader. All the information contained therein is incorporated herein by reference.

Materials and Methods

Recombinant enzymes—The catalytic domain of MMP-2 (amino acids 110-467 of GenBank Accession NO. NP_032636.1) was expressed under the T7 promoter in BL-21 cells. The cells were induced with 1 mM isopropyl-β-D-thiogalactopyranoside for 5 h. The cell pellet was resuspended in 50 mM Tris, pH 8.0, 0.5 mM EDTA, 50 mM NaCl, 5% glycerol and 1% Triton X-100 at a 1:25 ratio of the buffer to the original culture volume. The suspension was centrifuged for 10 min at 15,000 rpm, and the pellet was dissolved in 50 mM Tris, pH 8.0, 0.5 mM EDTA, 50 mM NaCl, 5% glycerol, and 0.2% Sarkosyl followed by a 30-min incubation on ice. The supernatant fraction was loaded onto a 5-ml gelatin-Sepharose column (prepacked, Amersham Biosciences), preequilibrated, and washed with dialysis buffer (50 mM Tris, pH 8.0, 50 mM NaCl, 5 mM $CaCl_2$, 10 µM $ZnCl_2$, 0.02% Brij). The protein was eluted with 50 mM Tris, pH 8.0, 1 M NaCl, 5 mM $CaCl_2$, 10 µM $ZnCl_2$, 0.02% Brij, and 15% Me2SO [Rosen, O., Inhibition of MMPs by Monoclonal Antibodies. 2001] and assayed using SDS-PAGE, and its catalytic activity was measured by fluorogenic peptide degradation [Knight, C.G., F. Willenbrock, and G. Murphy, A novel coumarin-labelled peptide for sensitive continuous assays of the matrix metalloproteinases. FEBS Lett, 1992. 296(3): p. 263-6].

Pro-MMP-9 [lacking the hinge region and the hemopexin domain, Ala]—Gly424|P14780|MMP9_HUMAN Matrix metalloproteinase-9 precursor (MMP-9) (EC 3.4.24.35)] was expressed in Escherichia coli ER2566 in a pTWIN expression vector and was purified to homogeneity from inclusion bodies as described earlier [Bjorklund, M., P. Heikkila, and E. Koivunen, Peptide inhibition of catalytic and noncatalytic activities of matrix metalloproteinase-9 blocks tumor cell migration and invasion. J Biol Chem, 2004. 279(28): p. 29589-97]. Pro-MMP-9 was activated with 1 mM p-aminophenylmercuric acetate (APMA, ICN Biomedicals Inc., Ohio, USA), dissolved in 200 mM Tris, for 30 min at 37° C.

Human recombinant pro-MMP-2 and pro-MMP-9, were expressed in HeLa S3 cells infected with the corresponding recombinant vaccinia viruses and purified to homogeneity as previously described [Olson, M. W., Gervasi, D. C., Mobashery, S., and Fridman, R. (1997) J. Biol. Chem. 272, 29975-29983; Fridman, R., Fuerst, T. R., Bird, R. E., Hoyhtya, M., Oelkuct, T. M., Kraus, S., Komarek, D., Liotta, L. A., Berman, M. L.; and Stetler-Stevenson, W. G. (1992) J. Biol. Chem. 267, 15398-15405].

Tetra-carboxy phenyl porphyrin Co(II)/Zn(II) (CoTCPP/ZnTCPP)—The ZnTCPP was synthesized by the reaction of $ZnCl_2$, and TCPP in N,N-dimethylformamide (DMF) as described [Harada, A., et al., Control of photoinduced electron transfer from zinc-porphyrin to methyl viologen by supramolecular formation between monoclonal antibody and zinc-porphyrin. Photochem Photobiol, 1999. 70(3): p. 298-302]. CoTCPP was synthesized by the reaction of $Co(OAc)_2 \cdot 4H_2O$ and TCPP in DMF as described [Harada, A., et al., Control of photoinduced electron transfer from zinc-porphyrin to methyl viologen by supramolecular formation between monoclonal antibody and zinc-porphyrin. Photochem Photobiol, 1999. 70(3): p. 298-302] and purified.

Synthesis of Imisdp—Described in Example 7 hereinbelow.

Hapten conjugation to protein—The haptens (4 mg) were activated for conjugation by adding 1,1'-Carbonyldiimidazole in DMF (at a molar ratio of 1:1) and incubating for 1 h. One to 50 moles of activated hapten were added to 20 mg/mL BSA or keyhole limpet hemocyanin (KLH) in 0.1 M carbonate buffer pH 8. The solution was stirred at room temperature for 3 h and then extensively dialyzed against PBS.

Immunization and Fusion—Each of adjuvant (KLH) conjugated CoTCPP, ZnTCPP or Imisdp were used to immunize BALB/c mice. Immunization and subsequent fusion to the NSO myeloma cell line were performed according to standard procedures [Harlow, E., and Lane, D., Using Antibodies: A Laboratory Manual Portable Protocol No. I. 1998].

Antibody Screening

ELISA—Supernatants of the growing hybridomas were screened for antibodies reactive with ZnTCPP, CoTCPP or Imisdp using direct ELISA in which respective hapten-BSA (3 µg/ml in PBS) was coated to Nunc maxisorp plates. The coating was performed at 4° C. overnight and incubation with antibodies at 20° C. for 1 h. HRP-conjugated anti-mouse mAb (Sigma) was used as the secondary antibody and 2,2'-azino-bis (3-ethylbenzthiazoline-6-sulphonic acid, ABTS, Sigma) was used as substrate. PBS containing 0.005% v/v Tween 20 (PBST) was used as washing reagent. The dilution buffer was PBS. $A_{602}$ was recorded by microplate reader in SPECTRAFluor Plus spectrometer (Tecan, Austria). As control supernatants were incubated with BSA coated plates in the same manner. Absorbance values above 0.5 millioptical density were considered as positive.

Competitive ELISA—Different dilutions of hybridoma supernatant were incubated with hapten-BSA coated plates following the steps described earlier. Titration curve was plotted and the titer dilution was determined at 50% of binding. Supernatants diluted to the titer concentration were pre-incubated with soluble ZnTCPP, CoTCPP or Imisdp compounds for 30 minutes and then transferred to hapten-coated microtiter plates following the steps described previously. The estimated dissociation constant was the concentration of soluble hapten required to attain 50% binding.

Production and purification—Selected hybridomas were subcloned twice by limited dilutions, followed by large-scale production by ascites tumors primed with pristine (2,6,10,14 tetrametylpentadecane) injected BALB/c mice. MAb were purified by the affinity chromatography on protein G Sepharose 4 Fast Flow (Amersham Biosciences). Ascites was centrifuged at 12,000 g for 15 min to remove the insoluble particles and lipid. The 1-mL ascites was diluted into 5 times volume with PBS then loaded to the 5-mL column volume protein G Sepharose. The elution peak was analyzed by SDS-PAGE.

Isotype determination—Culture supernatants obtained from cloned hybridomas grown in culture flasks were used as a source of mAb. Each antibody was isotyped by a Mouse Monoclonal Antibody Isotyping Kit (HyCult biotechnology b.v., The Netherlands).

Immunoblot analysis of purified antibodies—Purified antibodies were separated in 8% SDS-polyacrylamide gel, transferred to NC membranes (Bio-Rad), and subsequently subjected to immunoblot analysis using anti MMP-9 antibody (Sigma). The goat anti-mouse IgG conjugated with horseradish peroxidase (Sigma) was used as the secondary antibody. Signals were detected using ECL (Pierce).

Binding assay using purified proteins—MAbs (10 µg) were incubated with anti mouse IgG Agarose beads (Sigma) overnight at 4° C. in PBS. After washing unbound antibody, purified Pro-MMP-2, Pro-MMP-9 MMP-2 catalytic domain, MT1 catalytic domain or TACE (2 µg), were added following 2 h incubation at RT. The beads were collected by centrifugation and washed three times with PBS. The proteins that remained bound to the beads were eluted with SDS sample buffer, fractionated by SDS-PAGE, and detected by staining with Coomassie blue.

Immunoprecipitation and Western Blot—HT1080 cells were seeded in petri dishes. After reaching 80% confluence, the medium (DMEM supplemented with 10% FCS, nonessential amino acids, penicillin, streptomycin, sodium pyruvate, and L-glutamine) was changed to serum free medium (without FCS). Following another 24 h of incubation, conditioned medium (CM) was harvested from the adherent cells and concentrated using Millipore Centricon-10 (Bedford, Mass.). Concentrated supernatants were used for immunoprecipitations. CM was incubated with anti-1 (CoTCPP) mAb (15 µg/ml) overnight at 4° C. Protein A Sepharose (CL-4B Amersham Biosciences) was added to the samples and mixed for 2 h at RT. Beads were washed 3 times with PBS, suspended in SDS sample buffer, and heated to 95° C. for 3 min. Immunoprecipitates were recovered by centrifugation and subjected to SDS/PAGE. After separation, proteins were transferred to nitrocellulose (NC) membranes and probed with anti-MMP-2 antibody.

To activate ProMMP-2 produced by HT1080 cells, 1 mM of 4-aminophenyl mercuric acetate (APMA) was added to the concentrated CM followed by 6 h incubation in 37° C. After activation, the CM was dialyzed (x3) against PBS at 4° C., to remove APMA. Immunoprecipitation with the activated medium was performed as described above.

Binding to active MMP-9 using direct ELISA—MMP-9 Catalytic domain (2 µg/ml) was immobilized in microtiter wells. mAbs (1 mg/ml) were added to the wells following the same procedure as described for ELISA screen. anti MMP-9 antibody (Sigma) served as positive control and unrelated mouse IgG affinity purified from ascites served as negative control.

Kinetic assay—The enzymatic activity of MMPs was measured as described previously [ Solomon, A., et al., *Pronounced diversity in electronic and chemical properties between the catalytic zinc sites of tumor necrosis factor-alpha-converting enzyme and matrix metalloproteinases despite their high structural similarity*. J Biol Chem, 2004. 279(30): p. 31646-54]. The activity of MMP-9, MMP-2 and MT1-MMP was measured by monitoring the degradation of the fluorogenic peptide Mca-Pro-Leu-Gly-Leu-Dpa-Ala-Arg-NH$_2$ at $\lambda_{ex}$=340 nm and $\lambda_{em}$=390 nm as described by Knight et al. [FEBS Lett, 1992. 296(3): p. 263-6] purchased from Calbiochem-Novabiochem AG. The standard assay mixture contained 50 mM Tris buffer, pH 7.5, 200 mM NaCl, 5 mM CaCl$_2$, 20 µM ZnCl$_2$ and 0.05% Brij. The enzymatic activity of TACE was measured by monitoring the degradation of fluorogenic peptide QF-45 (Mca-Ser-Pro-Leu-Ala-Gln-Ala-Val-Arg-Ser-Ser-Ser-Arg-Lys(dinitrophenyl)-NH2) purchased from Calbiochem-Novabiochem AG.

In situ zymography—To localize net gelatinolytic activity of MMPs by in situ zymography, fluorescein isothiocyanate-labeled DQ gelatin that is intramolecularly quenched (Molecular Probes) was used as a substrate for degradation by gelatinases. Proteolysis by gelatinases yields cleaved fluorescein isothiocyanate-gelatin peptides and the localization of this fluorescence indicates the sites of net gelatinolytic activity. Briefly, Human fibrosarcoma HT1080 cells (which produce MMP-2,MMP-9 and MT1-MMP) were plated on 12-mm coverslips. After 24 h incubation, cells were treated with 1 uM of 13E11 mAb, for 30 min at 37° C. Untreated cells served as negative control for this experiment. Cells were washed with PBS and then incubated with zymography reaction buffer (0.05 M Tris-HCl, 0.15 M NaCl, 5 mM CaCl2, and 0.2 mM NaN3, pH 7.6, the high concentration of azide prevented the gelatin from being phagocytosed and thus allowing cell surface gelatinolytic activity to occur) containing 60 ug/ml DQ gelatin at 37° C. overnight. The zymography buffer contained 1 uM of the CoTCPP mAb for the treated cells. At the end of the incubation period, without fixation or further washes, gelatinolytic activity of the MMPs was localized and photographed by fluorescence microscopy and images were acquired by Spot digital camera.

Example 1

Conformational Mimcry of the Zinc Active Site by Small Organometalic Compounds

The zinc ion in the active site of MMPs is uniformly coordinated by three conserved histidine residues. During zymogen activation and substrate proteolysis zinc coordination varies from 4-coordination, tetrahedral geometry, in the non catalytic stages to 5-coordination, trigonal bipyramidal [Auld, D. S., Zinc coordination sphere in biochemical zinc sites. Biometals, 2001. 14(3-4): p. 271-313] in the catalytic stages. The conserved histidines can therefore assume different geometries with respect to the zinc ion. To sample these conformations, two compounds were selected as models for zinc environment mimicry Imisdp and Co/ZnTCPP (FIG. 1). Imisdp (synthesis is provided in Example 7 below) compound can mimic the 4-coordination geometry. In this case, a nearly tetrahedral conformation is formed by three imidazole bases and water molecule as the fourth ligand.

FIG. 2A shows an overlay of the constructed 3D model of the Imisdp molecule with the catalytic site of MMP-9 (PDB 1GKC) [Rowsell, S., et al., *Crystal structure of human MMP9 in complex with a reverse hydroxamate inhibitor*. J Mol Biol, 2002. 319(1): p. 173-81] that has been modified to represent the tetrahedral geometry of the zinc ligands. The modifications include replacing the ligand present in the X-ray structure (an hydroxamate inhibitor) with a water molecule and optimization of the full enzyme to a local minimum by a multilayer QM/MM approach (see materials and methods). High similarity exists between the calculated histidine zinc motif in MMP-9 and Imisdp in terms of distances of the Histidines' ε-nitrogen from the zinc ion (2.04±0.06 and 2.02 respectively) and the relative orientation of the three histidines toward the metal. The second molecule—Zn/CoTCPP, has four imidazole bases in coordination with zinc, or its analogous metal cobalt, in a co-planar conformation with respect to the metal ion [Stevens, E. D., *Electronic Structure of Metalloporphyrins.* 1. *Experimental Electron Density Distribution of (meso-Tetraphenylporphinato)cobalt (II)*. J. Am. Chem. SOC, 1981. 103(17): p. 5087-5095]. This configuration imitates the conformation of two of the three histidines in 5-coordination trigonal bipyramidal geometry where metal is almost coplanar with the two histidines which form the base of the pyramid. FIG. 2B shows the crystal structure of MMP-9 (PDB 1GKC) where the zinc is coordinated by 5 ligands (two additional ligands are contributed by the hydroxamate inhibitor) the orientation of the two histidines at the base of the pyramid and their distances from the zinc ion (2.2±0.02, 2.03±0.04 and 1.95 for MMP-9, ZnTCPP and CoTCPP respectively) are comparable to Co/ZnTCPP molecule.

Example 2

Monoclonal Antibodies Generation and Selection

Monoclonal antibodies against CoTCPP, ZnTCPP and Imisdp (FIG. 1) were produced by immunization of mice and selection of specific antibodies by an ELISA screen with the respective compound as the coated antigen. Three antibodies were selected for extensive study. Notably, these clones were chosen because they displayed the best affinity toward their immunizing hapten respectively, based on competitive ELISA screen. Their binding constants, ranging from 0.01-0.09 μM, (Table 3, below), are characteristic of high affinity mAbs. MAbs were propagated as ascites in mice and purified with protein G beads.

TABLE 3 summary of isotype and ELISA competition analysis of anti-CoTCPP, ZnTCPP and Imisdp monoclonal antibodies.

| Immunizing Hapten | Antibody Isotype | Kd [μM]* | Name |
|---|---|---|---|
| CoTCPP | IgG2b | 0.09 | 13E11 |
| ZnTCPP | IgG2a | 0.01 | 15E12 |
| Imisdp | IgG2a | 0.09 | 6C6 |

*Binding affinities (Kd) of the antibodies toward their immunizing hapten were determined by competitive ELISA (for details, see Materials and Methods).

Example 3

Monoclonal Antibodies Cross React with MMP-2 and MMP-9

To determine whether mAbs raised against synthetic compounds that mimic the zinc histidine conformation in the catalytic site of MMPs, cross react with the exposed zinc histidine motif within the active sites of MMP-2 and MMP-9, monoclonal antibodies were first screened for binding MMP-9 using direct ELISA.

The three mAbs bound MMP-9 catalytic domain directly adsorbed to microtiter plate wells (commercial anti MMP-9 antibody served as positive control and unrelated IgG served as negative control). Interestingly, mAbs that have been propogated as ascites in mice co purified with active MMP-9 present in mice ascites fluid. Western blot analysis, of the purified antibodies alone, with anti MMP-9 antibody as the primary antibody showed a clear band corresponding to the expected molecular mass of about 82 KDa for active MMP-9. Thus, mAbs formed a complex in vivo with the native enzyme.

Monoclonal antibodies were next screened for binding MMP-2 using Immuno Affinity based assay. Antibodies were incubated with MMP-2 catalytic domain (MMP-2cat) in vitro, followed by pull down with anti mouse IgG Agarose beads. As FIG. 3A shows, all mAbs bound MMP-2 cat.

To establish that binding occurs through direct interaction with the active site, mAbs were analyzed for their ability to bind Pro-MMP-2 and Pro-MMP-9. In the latent enzymes the pro domain structure shields the catalytic cleft. Hence, blocking of the active site by the pro-domain structure should prevent mAbs binding, providing it recognizes the histidine zinc motif within the active site. Under the same conditions, no binding to the pro enzymes was detected (FIG. 3B). This mode of binding to active MMP-2 but not to Pro-MMP-2 was further challenged in an in vivo like environment with full length native MMP-2 secreted by human fibrosarcoma (HT1080) cell cultures. Immunoprecipitation of HT1080 conditioned medium with anti-CoTCPP antibody followed by western blot analysis showed binding to active but not Pro-MMP-2 (FIG. 3C). These results demonstrate that all three antibodies cross react with MMP-2 and MMP-9. Exposure of the active site cleft is essential for antibody binding, confirming that mAbs interact directly with the active sites of MMP-2 and 9.

Example 4

Anti CoTCPP and Anti Imisdp mAbs Inhibit MMP-2 and MMP-9 In-Vitro

Anti Imisdp and anti CoTCPP mabs inhibited the proteolytic activity of MMP-2 and MMP-9 in the micromolar range (FIG. 5). Kinetic analysis of the inhibition of MMPs by mAbs was performed in a continuous fluorometric assay with a quenched fluorescent peptide substrate. Surprisingly anti ZnTCPP mAb did not show inhibitory effect.

To determine the nature of the inhibition by anti CoTCPP mAb, experiments were carried out using enzymes in the presence or absence of mAb with different concentrations of fluorescent peptide substrate. The data presented in a Lineweaver-Burk plot shown in FIGS. 4A-B is characteristic of competitive inhibition profile with Ki values of 13 μM and 24 μM for MMP-9 and MMP-2 respectively. The competitive inhibition profile indicated that the mAb bound to the same site as the peptide substrate. This mode of inhibition is a further verification of the direct interaction with the active site. Remarkably, Anti Imisdp mAb showed concentration-dependent inhibitory effect toward MMP-2 and MMP-9, assuming competitive inhibition, calculated Ki's are 5.8 μM and 3 μM toward MMP-9 and MMP-2 respectively (FIG. 5). Since mAbs recognize the binding site of MMP-2 and MMP-9, further optimization of the interface complementarities between the mAbs and MMPs, both structurally and electrostatically is achievable by affinity maturation methods (Paul J. Carter Nature Reviews Immun. Vol. 6 2006 343-357). Using this approach may lead to highly specific inhibitors, that will take advantage of specificity features that are either inside or outside the active site.

Example 5

In Situ Zymography

To confirm the inhibitory activity of anti CoTCPP mAb at cellular level, the effect of the antibody was examined on gelatinolytic activity of human fibrosarcoma HT1080 cells that constitutively secrete MMP-2 and 9 by in situ zymography. To localize gelatinolytic activity of MMPs by in situ zymography, fluorescein isothiocyanate-labeled gelatin that is intramolecularly quenched (DQ-gelatin) was used as substrate. Proteolysis by gelatinases yields cleaved fluorescein isothiocyanate-gelatin peptides and the localization of this fluorescence indicates the sites of net gelatinolytic activity.

Untreated human fibrosarcoma HT1080 cells (FIG. 7A) exhibited significant cell surface gelatinolytic activity. In the presence of 1 μM mAb (FIG. 7B), gelatinase activity was reduced as compared to that observed in control cells. These results demonstrate that anti CoTCPP mAb inhibited MMP-2 and MMP-9 at the cellular level.

Example 6

Selectivity of mAbs of the Present Invention

The antibody selectivity was tested by examining the binding and inhibitory effect of anti CoTCPP and anti Imisdp mAbs toward MMP-14 (MT1-MMP) and TNF-α-converting enzyme (TACE) a zinc-dependent metalloproteinase belonging to the related ADAM (a disintegrin and metalloproteinase) family (ADAM-17). Inhibitory effect toward MT1-MMP and TACE was tested by in-vitro fluorescence enzymatic activity assay with the appropriate peptide substrates. Anti CoTCPP mAb showed no inhibitory effect toward MT1-MMP or TACE. To determine whether it binds TACE and MT1-MMP without consequential inhibition, immuno affinity based experiments were performed with the purified enzymes, yet no binding was detected. In contrast to anti CoTCPP mAb, anti Imisdp mAb inhibited MT1-MMP, with Ki value of 10 μM but did not display inhibitory effect toward TACE. Results are listed in Table 4 below.

TABLE 4

| MMP | 6C6 ($IC_{50}$ μM) | 13E11 (IC50 μM) | 15E12 (IC50 μM) |
|---|---|---|---|
| MMP-2 | 3 ± 0.2 | 24 ± 1 | NI |
| MMP-9 | 4.5 ± 0.2 | 15 ± 0.8 | NI |
| MT1-MMP | 14.4 ± 0.7 | NI | NI |
| TACE | NI | NI | NI |

NI, "not inhibiting" at concentrations up to 30 μM

High structural similarity at the active site exists among MMP family members and TACE specifically the three-dimensional structural elements surrounding the zinc-binding site are almost identical, due to the need to accommodate the substrates' peptide backbone and the presence of conserved zinc-binding motif EXXHXXGXX1-1 [Solomon, A., et al., *Pronounced diversity in electronic and chemical properties between the catalytic zinc sites of tumor necrosis factor-alpha-converting enzyme and matrix metalloproteinases despite their high structural similarity*. J Biol Chem, 2004. 279(30): p. 31646-54; Lukacova, V., et al., *A comparison of the binding sites of matrix metalloproteinases and tumor necrosis factor-alpha converting enzyme: implications for selectivity*. J Med Chem, 2005. 48(7): p. 2361-70]. Therefore mAb selectivity among MMPs is not expected based solely on recognition of the conserved histidine zinc motif. However, unlike small molecular weight synthetic inhibitors, an antibody being a large protein molecule must have limited accessibility towards an active site cleft that is buried within the framework of the protein. Particularly since mAbs were shown to specifically interact with the catalytic zinc ion, the degree of exposure of the zinc ion to solution must be critical for antibody binding. MT1-MMP and to a larger extent TACE are distinguished by a deep Si pocket correlated with relatively buried catalytic zinc ion as exhibited by their crystal structures. This difference in the depth of the active site may account for antibodies' lack of inhibitory effect toward TACE. These results suggest that selectivity may be achieved based on the degree of exposure of the catalytic zinc ion. Another important factor that should be considered when comparing MMPs and TACE, are differences in the active site pocket in terms of chemistry such as hydrophobicity and polarity (see FIG. 8). The active site of TACE for example, is significantly more polar than the active sites of most MMPs. Solomon et al demonstrated that such variation in the polarity of the active site directly influence the orientation of the active site histidine imidazole rings toward the catalytic zinc ion [Solomon, A., et al., *Pronounced diversity in electronic and chemical properties between the catalytic zinc sites of tumor necrosis factor-alpha-converting enzyme and matrix metalloproteinases despite their high structural similarity*. J Biol Chem, 2004. 279(30): p. 31646-54].

The selectivity of anti CoTCPP and anti Imisdp was further challenged, by testing their cross reactivity with non related zinc dependent enzymes—Carbonic Anhydrase (CA) and brockii alcohol dehydrogenase (TbADH). Similar to active MMPs CA contains a zinc ion that is tetrahedraly coordinated to three histidine residues and a water molecule, TbADH contains a catalytic zinc ion that is tetraheadrally coordinated to four different amino acid residues, histidine, cysteine, aspartate and glutamate. Appropriate in vitro functional inhibition experiments, as well as similar immuno affinity based experiments were performed to examine cross reactivity with these enzymes, however no binding or inhibition was observed. Anti CoTCPP mAb was also tested for its cross reactivity with related physiological porphyrins such as the Heme group within Myoglobin and Hemoglobin and vitamin. No cross was detected in competitive ELISA as well as immuno affinity assay.

Carbonic anhydrase, and alcohol dehydrogenase all have rather buried active sites, similarly, the porphyrin moiety in Myoglobin and Hemoglobin is not exposed. Vitamin B12 contains metal at the center of planer imidazol structure yet the axial ligands may interfere with the binding of the mAb. Altogether these results substantiate that anti CoTCPP mAb recognizes relatively exposed metal-imidazole configuration with no interference of axial metal-coordinating residues.

Example 7

Synthesis of [2-(2-minoethylcarbomoyl)-ethoxymethyl]-tris-[2-(N-(3-imidazol-1-yl-propyl))-ethoxymethyl]methane Zinc(II) (3), FIG. 9

(i) Synthesis of Tetra(2-pentachloro-phenoxycarbonyl-ethoxymethyl)methane:

Synthesis of pentachlorophenol-substitution tetra-active ester was carried out as in the procedure of Haim Weizmann et al., JACS 1996, 118, 12368-12375.

(a) Prepration of mono-substituted tri active ester: Tetra active ester (1) (1 g, 0.69 mmol) and BocNHCH$_2$CH$_2$NH$_2$ (100 mg, 0.62 mmol) were dissolved in 20 ml of dry dichloromethane. The solution was stirred overnight while maintain pH~8 with triethyl amine. The solution was concentrated and purified by flash chromatography with CHCl$_3$ :ethylacetate (90:10) to give (152 mg, 15% yield). $^1$H NMR 250MHz (CDCl$_3$) δ: 1.4(s, 9H, Boc); 2.4 (t, 2H, J=6 Hz, —CH$_2$—CH$_2$—CONH); 2.9 (t, 6H, J=6 Hz, —CH$_2$—CH$_2$—COOPCP); 3.2 (q, 2H, J=6 Hz, —CONH—CH$_2$—CH$_2$—NHBoc); 3.31(t, 2H, J=6 Hz, —CONH—CH$_2$—CH$_2$—NHBoc); 3.38(s, 2H, —C—CH$_2$—O—CH$_2$—CH$_2$—CONH—); 3.42(s, 6H, —C—CH$_2$—O—CH$_2$—CH$_2$—COOPCP); 3.61(t, 2H, J=6 Hz, —C—CH$_2$—O—CH$_2$—CH$_2$—CONH—); 3.78(t, 6H, J=6 Hz, —C—CH$_2$—O—CH$_2$—CH$_2$—CONH—); 5.03(t, 1H, NH); 6.7(t, 1H, NH).

(b) Preparation of tris (imidazole): The mono-substituted triactive ester (150 mg, 0.11 mmol) and 1-(3-aminopropyl)-imidazole (33 µlt, 0.39 mmol) were dissolved in (20 ml) dry THF and stirred overnight at room temparture. The white color solution was concentrated and purified by column chromatography using silica of (0.063-0.200 mm) with CHCl$_3$: methanol(50-90%) to give (45 mg 44% yield). $^1$H NMR 250 MHz (CDCl$_3$/MeOD) δ: 1.45(s, 9H, Boc); 2.0(m, 6H, J=6 Hz, —CONH—CH$_2$—CH$_2$—CH$_2$-imi); 2.4(t, 6H, J=6 Hz, —O—CH$_2$—CH$_2$—CONH—); 2.5 (t, 2H, J=6 Hz, —CH$_2$—CH$_2$—CONH—CH$_2$—CH$_2$—NHBoc) 3.0 (m, 8H, J=6 Hz, —CONH—CH$_2$—CH$_2$—CH$_2$-imi, —CH$_2$—CH$_2$—CONH—CH$_2$—CH$_2$—NHBoc); 3.1(t, 2H, J=6 Hz, —CONH—CH$_2$—CH$_2$—NHBoc); 3.4 (b, 8H, —C—CH$_2$—O—CH$_2$—CH$_2$—CONH—CH$_2$—CH$_2$—NHBoc, —C—CH$_2$—O—CH$_2$—CH$_2$—CONH—); 3.6 (m, 8H, J=6 Hz, —C—CH$_2$—O—CH$_2$—CH$_2$—CONH—, —C—CH$_2$—O—CH$_2$—CH$_2$—CONH—CH$_2$—CH$_2$—NHBoc,); 4.0 (t, 6H, J=6 Hz, —CONH—CH$_2$—CH$_2$—CH$_2$—imi); 5.5(t, 1H, NH); 6.98(s, 3H, Imi); 7.06(s, 3H, Imi) 7.32(t, 3H, NH); 7.57(s, 3H, Imi). ESI-MS : 910.87[M+Na]$^+$, 925.98 [M+K]$^+$.

(c) Preparation of tris(imidazole) with free amine (2): Tris (imidazole) (40 mg, 0.045 mmol) was dissolved in 6 ml of dichloromethane and trifluroacitic acid (2:1) mixture and stirred for an hour. The reaction mixture was concentrated and evaporated several times with carbon tetrachloride and dried under high vacuum to remove TFA from the mixture to obtain (30 mg, 85% yield, b). $^1$H NMR 250MHz (CDCl$_3$/MeOD) δ: 1.9 (m, 6H, J=6 Hz, —CONH—CH$_2$—CH$_2$—CH$_2$-imi); 2.3 (m, 8H, J=6 Hz, —O—CH$_2$—CH$_2$—CONH—, —CH$_2$—CH$_2$—CONH—CH$_2$—CH$_2$—NH$_2$); 2.9 (t, 2H, J=6 Hz, —CONH—CH$_2$—CH$_2$—CH$_2$-imi); 3.0 (t, 2H, J=14Hz, —CONH—CH$_2$—CH$_2$—NH$_2$); 3.31(t, 2H, J=6 Hz, —CH$_2$—CH$_2$—CONH—CH$_2$—CH$_2$—NH$_2$); 3.4 (b, 8H, —C—CH$_2$—O—CH$_2$—CH$_2$—CONH—CH$_2$—CH$_2$—NH$_2$, —C—CH$_2$—O—CH$_2$—CH$_2$—CONH—); 3.6 (m, 8H, J=6 Hz, —C—CH$_2$—O—CH$_2$—CH$_2$—CONH—, —C—CH$_2$—O—CH$_2$—CH$_2$—CONH—CH$_2$—CH$_2$—NH$_2$); 4.0 (t, 6H, J=6 Hz, —CONH—CH$_2$—CH$_2$—CH$_2$-imi); 7.26(s, 3H, Imi); 7.32(s, 3H, Imi); 8.82(s, 3H, Imi).

3. Preparation of tris(imidazole)-Zn(II) complex (3) : Compound 2 (30 mg, 0.038 mmol) was dissolved in 1 ml of methanol. To this 2-3 drops of 1N NaOH solution and ZnCl$_2$ (5 mg, 0.04 mmol) was added and stirred for half an hour. The white color precipitate was filtered to obtain (12 mg, 37% yield). $^1$H NMR 250 MHz (MeOD/D$_2$O) δ: 1.8 (m, 6H, J=6 Hz, —CONH—CH$_2$—CH$_2$—CH$_2$-imi); 2.4 (m, 8H, J=6 Hz, —O—CH$_2$—CH$_2$—CONH—, —CH$_2$—CH$_2$—CONH—CH$_2$—CH$_2$—NH$_2$); 3.0 (t, 2H, J=6 Hz, —CONH—CH$_2$—CH$_2$-imi); 3.0 (t, 2H, J=6 Hz, —CONH—CH$_2$—CH$_2$—NH$_2$); 3.31(b, 2H, —CH$_2$—CH$_2$—CONH—CH$_2$—CH$_2$—NH$_2$); 3.4 (b, 8H, —C—CH$_2$—O—CH$_2$—CH$_2$—CONH—CH$_2$—CH$_2$—NH$_2$, —C—CH$_2$—O—CH$_2$—CH$_2$—CONH—); 3.6 (m, 8H, —C—CH$_2$—O—CH$_2$—CH$_2$—CONH—, —C—CH$_2$—O—CH$_2$—CH$_2$—CONH—CH$_2$—CH$_2$—NH$_2$); 4.2 (b, 6H, —CONH—CH$_2$—CH$_2$—CH$_2$-imi); 7.19(s, 3H, Imi); 7.28(s, 3H, Imi); 8.55(s, 3H, Imi). ESI-MS :852.09[M+1]$^+$.

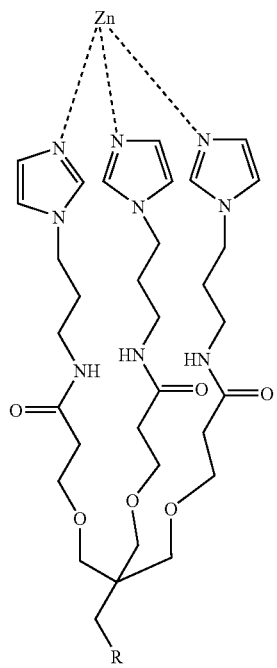

R=O—CH$_2$—CH$_2$—CONH—CH$_2$—CH$_2$—NH$_2$

[2-(2-minoethylcarbomoyl)-ethoxymethyl]-tris-[2-(N-(3-imidazol-1-yl-propyl))-ethoxymethyl] methane.

Example 8

6C6 Cross Reacted with the Catalytic Sites of Gelatinases

It was discovered that some amount of 6C6 had co-purified with active MMP9 from ascitic fluid. The presence of detectable amounts of MMP9 in ascetic tumor, induced in mice to propagate mAbs was revealed by Western blot and gelatin zymography (data not shown). MMP9-antibody complex was purified from mouse ascites fluid using Protein G affinity chromatography (Protein G binds to the antibody's constant domain, leaving the variable domain free to interact with the antigen). As shown in FIG. 11A, co-purified MMP9 was detected by western blotting purified 6C6-MMP9 complex using comercially available anti-MMP9 antibody. A band with molecular weight of ~82 kDa, corresponding to active MMP9 lacking the pro-domain was identified. This band was not detected in irrelevant mouse mAb control that was purified and analyzed in the same manner. These results showed that 6C6 formed a specific in vivo complex with endogenous, active, mouse MMP9.

To further check for binding to the active form of highly homologous MMP2 enzyme, analogous immunoprecipitation experiments were performed in vitro. 6C6 was incubated with purified MMP2 catalytic fragment in 3:1 molar ratio. SDS-PAGE analysis of protein A sepharose immunoprecipitates, revealed formation of a specific complex of 6C6 with active MMP2 catalytic fragment (FIG. 11B). Protein A beads alone did not immunoprecipitate MMP2. Next, binding to the inactive zymogenic (latent) forms of MMP2 and 9 was tested. As all MMPs are produced as inactive zymogens, they have N-terminal propeptides of approximately 80-90 amino acids that block the active sites [Bode, W. and K. Maskos, Biol Chem, 2003. 384(6): p. 863-72] (FIG. 11D). Immunoprecipitation experiments with pro-MMP2 and 9 were performed in a similar manner. Importantly, the antibody did not bind to the latent enzyme (FIG. 11C). Significantly, 6C6 bound only to the active enzyme conformation in which the active site zinc protein complex is exposed to solution.

These results confirmed that 6C6 antibody, raised and screened against active-site-mimic bioinorganic hapten cross reacted with the protein active sites of MMP2 and 9. Apparently, the zinc-tripod hapten was able to mimic the three-dimensional structure of the respective zinc-histidine epitope in the native protein. Remarkably, recognition of this minimal metal-protein structural epitope was enough to elicit cross reactivity with the native enzyme. Binding only to the activated enzymes and not their latent form in which the pro domain blocked access to the catalytic zinc protein epitope (FIG. 11D), indicated direct interaction of 6C6 with the zinc catalytic site. Notably, 6C6 bound native MMP9 in vivo demonstrating that the antibody can form a specific complex with the enzyme in a complex protein environment.

Discerning the activated enzyme species from the latent form is unique and valuable functional property of 6C6. This activity is unique to 6C6, as opposed to other antibodies raised against MMP9. This is because immunization with proteins typically yields epitopes directed toward surface loops, while the catalytic amino acids are mostly buried inside a cleft on the enzyme's surface. This part of the molecule is regarded to be of low immunogenicity. Hence, neutralizing monoclonal antibodies raised by conventional methods (against native proteins or protein fragments) generally interact with regions contiguous or adjacent to the active site rather then the active site catalytic residues and inhibit via steric hindrance mechanism. Such antibodies typically bind to the inactive precursor as well as the active form. The present unique active-site-mimic hapten immunization approach may have enabled the production of antibodies that recognize the catalytic metal protein residues in MMPs, which is not attainable by a conventional protein immunization approach.

Example 9

6C6 Selectively Inhibit Gelatinases In Vitro and In Situ

To determine the enzyme-inhibiting capacity of 6C6 towards MMP9 and MMP2, inhibition assays were performed using small fluorogenic peptide substrates (7 amino acids) that spans the active site cleft of gelatinases. The initial reaction velocities were measured for several concentrations of the mAb. 6C6 inhibited the catalytic activity of both enzymes (FIGS. 12A-B). Competitive mechanism of inhibition was determined by analyzing MMP9 activity in the presence of various concentrations of inhibitory antibody, as a function of substrate concentration. The data shown in FIG. 12A in the form of double reciprocal Linweaver-Burk plot, demonstrates competitive inhibition profile. Fitting the inhibition data to equation of competitive inhibition systems, Ki of 1±0.1 µM and 1.4±0.16 µM for MMP9 and 2 respectively was obtained. It was also determined that 6C6 was not cleaved by MMP-9 after overnight incubations with high concentrations (30 µM) of MMP9, demonstrating that the observed inhibition of MMP9 by 6C6 was not due to cleavage of competitor substrate. The kinetic analysis of MMP9 was taken as representative of inhibition mechanism by 6C6 as it was designed to recognize the same epitope in the different MMPs. Inhibitory effect was consistent for catalytic fragment species of MMP2 and 9 as well as full length enzyme forms of gelatinases. Specifically, recombinant MMP9 and MMP2 catalytic fragments, containing the catalytic domain as well as fibronectin domain but not the hemopexin domain; as well as MMP9 recombinant minimal catalytic unit containing only the catalytic domain and lacking both fibronectin and hemopexin domain were all inhibited similarly to full length (p-aminophenylmercuric acetate (APMA) activated) gelatinases purified from the media of HeLa S3 cells infected with a recombinant vaccinia virus encoding the full-length cDNA of human pro-MMP2 and 9 as described previously [Olson, M.W., et al., J Biol Chem, 2000. 275(4): p. 2661-8]. These results confirmed that inhibition is mediated by direct interaction with the catalytic domain and is not dependent on interaction with either the hemopexin or the fibronectin domains. The competitive inhibition profile provided a further indication of direct interaction with the catalytic zinc site. A non relevant mAb prepared in a similar manner did not interfere with the enzyme's photolytic activity. Thus, the observed inhibition was not due to trace amounts of co-purified contaminants. Antibodies for these experiments were purified from tissue culture and did not contain detectable amounts of active MMP9 in the purified antibody fraction.

To explore the selectivity of 6C6, its reactivity was tested toward different matrix metalloproteinase subgroups including matrilysin (MMP7), membrane type MMP (MT1-MMP) and related disintegrin (ADAMs) tumor necrosis factor-α-converting enzyme (TACE). The core structures of these enzymes, are highly similar, varying mostly within the peripheral loops. Specifically the zinc-histidine scaffold is well conserved, showing a consensus helix followed by a loop that serves as a scaffold for the three histidine residues that coordinate the catalytic zinc ion (FIG. 13).

Similar inhibition assays were performed with appropriate flourogenic peptide substrates. Interestingly, neither MMP-7 nor TACE were inhibited to any measurable extent upon incubation with 6C6 at concentrations of up to 30 µM, indicating a substantial level of selectivity toward gelatinases. MT1-MMP was inhibited by 6C6, less potently, with Ki of 14.4±0.75 µM. Interestingly, the origin of this selectivity can not be elucidated based exclusively on the antibody's design to recognize the conserved zinc-histidine scaffold since the core structures particularly in the active site are highly similar. Sequence variations, mostly within the peripheral loops dictate differences in the extent of exposure of the zinc-histidine motif, in the shape of the active site and its surface electrostatic may account for this selective inhibitory pattern.

6C6 was also tested for cross reactivity with different zinc dependent metallo-proteases, Carbonic Anhydrase and Alcohol Dehydrogenase. Analogous to MMPs, Carbonic Anhydrase (CA) has a catalytic zinc ion tetrahedraly coordinated to three histidine ligands and a water molecule. Consequently, several potent small molecule MMP inhibitors (of the sulfonylated amino acid hydroxamate type) also act as efficient CA inhibitors and vice versa. Some N-hydroxysulfonamides investigated previously as CA inhibitors also show inhibitory properties against MMPs [Scozzafava, A. and C. T. Supuran, J Med Chem, 2000. 43(20): p. 3677-87]. The active site of Alcohol Dehydrogenase from thermophilic bacterium (TbADH) includes a different zinc-protein moiety in which zinc is bound to histidine, cysteine, aspartate and glutamate located inside a crevice. Appropriate functional inhibition experiments in the presence of mAb concentrations up to 30 µM, displayed no inhibitory effect toward both enzymes. Notably, the active site of CA, located in the central region of a 10-stranded, twisted β-sheet, is comprised of cone-shaped cleft, 15 Å deep, with the tetrahedral $Zn^{2+}$ ion at the bottom of the cleft. Unlike small molecule inhibitors, the zinc ion must be too deeply buried for interaction with an antibody. Importantly these experiments further demonstrate selective inhibitory profile of 6C6.

At the cellular environment, the inhibitory effect of 6C6 toward gelatinases was further tested using gelatinases' natural substrate—gelatin, by in situ zymography. Human fibrosarcoma, HT 1080 cells, grown in culture expressing membrane bound MT1-MMP and secreting MMP-2 and 9 [Giambernardi, T. A., et al., Matrix Biol, 1998. 16(8): p. 483-96] were overlaid with fluorescein-conjugated gelatin (DQ gelatin). As shown in FIGS. 14A-C, untreated HT1080 cells exhibited significant cell surface gelatinolytic activity. Treatment with 5 µM mAb significantly decreased surface gelatinolytic activity, analogous to inhibition observed with mechanism based gelatinase inhibitor, SB-3CT. SB-3CT has analogous inhibitory profile, as it inhibits both gelatinases and MT1-MMP (Ki values are 28, 400, and 110 nM for MMP2, MMP9 and MT1-MMP respectively).

In summary 6C6 inhibited both synthetic peptide cleavage in vitro and natural macromolecular substrate in situ. 6C6 displayed competitive mode of inhibition toward MMP9, analogous to TIMP's mechanism of inhibition. Competitive inhibitory profile is a further indication of direct interaction with the catalytic zinc moiety. Importantly, 6C6 showed selective inhibitory profile toward gelatinases. The origin of this selectivity cannot be explained by the antibody targeting of the conserved zinc-histidine motif. These results suggest that the antibody interacts with additional determinants on the enzyme's surface that account for the observed specificity.

Example 10

Effect of 6C6 MAb Treatment on DSS-Induced Colitis in Mice

There is growing evidence that MMPs are implicated in tissue remodeling and destruction associated with several inflammatory conditions, including inflammatory bowel disease (IBD) [Baugh, M. D., et al., Gastroenterology, 1999. 117(4): p. 814-22; Heuschkel, R. B., et al., Gut, 2000. 47(1): p. 57-62; von Lampe, B., et al., Gut, 2000. 47(1): p. 63-73; Kirkegaard, T., et al., Gut, 2004. 53(5): p. 701-9].

Therefore, the present inventors examined the anti gelatinase inhibitory effect of 6C6 in vivo in mice experimental model of inflammatory bowel disease.

To explore the inhibitory activity of 6C6, the ability of mAb treatment to ameliorate DSS induced acute colitis was examined. Specifically, 2% DSS was provided to the highly susceptible mouse strain C57BL/6 for five days. 6C6 treatment was given daily by intraperitoneal injections of 1.5 or 5 mg/mouse, starting at the day of induction. Mice exposed to 2% DSS developed symptoms of acute colitis, with diarrhea, rectal bleeding and severe weight loss.

The effect of mAb treatment on the daily monitored disease activity index (DAI), (combined score of body weight, bleeding and stool consistency) is shown in FIG. 15A. MAb treated mice had decreased disease activity compared to control (significant from day 6). An additional macroscopic manifestation of DSS-induced colitis is the reduction in colon length (FIG. 15B). Thus 30% decrease in colonic length was found in untreated mice in comparison with naive mice, 11 days after DSS induction. In contrast only an average of 22% or 16% reduction was obtained in 6C6-treated mice dosed with 1.5 and 5 mg/kg mouse respectively. The protective effects of 6C6 were also confirmed by the mortality rate from the disease. Mortality rate of 60% was found in the untreated mice, 11 days after induction, whereas only a 33% mortality rate was observed in the 6C6 treated mice (FIG. 15C). Thus, treatment of C57BL/6 mice with 6C6 resulted in improved survival rate, in addition to the reduced manifestations of DSS-induced colitis.

Overall, these results demonstrated the therapeutic potential of 6C6 as gelatinase inhibitor.

Example 11

Characterization of the MMP9-6C6 mAb Complex by X-Ray Absorption Spectroscopy

In order to further study the differences between active MMP9 and an inhibited MMP9-6C6 complex, X ray, absorption spectroscopy was performed. FIG. 16 shows the fluorescence XAS data collected. The data is presented in the form of Fourier transform (FT) spectra to provide the radial distribution of the various atoms within the first and second coordination shells of the catalytic zinc ion in MMP9. Apparent change in the radial distribution spectra of the free and inhibited enzyme can be observed above the noise level. These spectral changes indicate that the local environment of the catalytic zinc ion undergoes structural changes upon binding to 6C6. The observed deviation in both spatial distribution and peak intensities of the FT spectral features between the active and the inhibited enzyme indicate unequivocally that the local structure of the catalytic zinc changes upon mAb complex formation.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims. All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention.

REFERENCE LIST (Additional References are Cited in the Text)
1. Nagase, H. and Woessner, J. F. Jr. (1999). Matrix metalloproteiases.Minireview. J. Biol. Chem. 274: 21491-21494.
2. Bode, W., Fernandez-Catalan, C., Nagase, H., and Maskos, K. (1999). Endoproteinase-protein inhibitor interactions. APMIS 107, 3-10.
3. Bode, W., Fernandez-Catalan, C., Tschesche, H., Grams, F., Nagase, H., and Maskos, K. (1999). Structural properties of matrix metalloproteinases. Cell. Mol. Life. Sci. 55, 639-652.
4. Borkakoti, N. (1998). Matrix metalloproteases: variations on a theme. Prog. Biophys. Mol. Biol. 70, 73-94.
5. Brown, S., Bernardo, M. M., Li, Z. H., Kotra, L. P., Tanaka, Y., Fridman, R., and Mobashery, S. (2000). Potent and Selective Mechanism-Based Inhibition of Gelatinases. J. Am. Chem. Soc., 122, 6799 -6800.
6. Fridman, R., Fuerst, T. R., Bird, R. E., Hoyhtya, M., Oelkuct, M., Kraus, S., Komarek, D., Liotta, L. A., Berman, M. L., and Stetler-Stevenson, W. G. (1992). Domain structure of human 72-kDa gelatinase/type IV collagenase. Characterization of proteolytic activity and identification of the tissue inhibitor of metalloproteinase-2 (TIMP-2) binding regions. J Biol. Chem. 267, 15398-405.
7. Gogly, B., Groult, N., Hornebeck, W., Godeau, G., and Pellat, B. (1998). Collagen Zymography as a Sensitive and Specific Technique for the Determination of Subpicogram Levels of Interstitial Collagenase. Anal. Biochem. 255, 211-216.
8. Gomez, D. E., Alonso, D. F., Yoshiji, H., and Thorgeirsson, U. P. (1997). Tissue inhibitors of metalloproteinases: structure, regulation and biological functions. Eur. J. Cell. Biol. 74, 111-122.
9. Henriet, P., Blavier, L., and Declerck, Y. A. (1999). Tissue inhibitors of metalloproteinases (TIMP) in invasion and proliferation. APMIS 107, 111-119.
10. Kleifeld, O., Kotra, L. P., Gervasi, D. C., Brown, S., Bernardo, M. M., Fridman, R., Mobashery, S., and Sagi, I. (2001). X-ray Absorption Studies of Human Matrix Metalloproteinase-2 (MMP-2) Bound to a Highly Selective Mechanism-based Inhibitor. Comparison with the latent and active forms of the enzyme. J. Biol. Chem. 276, 17125-17131.
11. Korkhin, Y., Kalb(Gilboa), A. J., Peretz, M., Bogin, O., Burstein, Y., and Frolow, F. (1998). NADP-dependent Bacterial Alcohol Dehydrogenases: Crystal Structure, Cofactor-binding and Cofactor Specificity of the ADHs of Clostridium beijerinckii and Thermoanaerobacter brockii. J. Mol. Biol. 278, 967-981.
12. Morgunova, E., Tuuttila, A., Bergmann, U., Isupov, M., Lindqvist, Y., Schneider, G., and Tryggvason, K. (1999). Structure of Human Pro-Matrix Metalloproteinase-2: Activation Mechanism Revealed. Science 284, 1667-1670.
13. Bode, W., Fernandez-Catalan, C., Tschesche, H., Grams, F., Nagase, H., and Maskos, K. (1999). Structural properties of matrix metalloproteinases. Cell. Mol. Life. Sci. 55, 639-652.
14. Netzel-Arnett, S., Mallya, S. K., Nagase, H., Birkedal-Hansen, H., and Van Wart, H. E. (1991). Continuously recording fluorescent assays optimized for five human matrix metalloproteinases. Anal. Biochem. 195, 86-92.
15. Rehr, J. J., Mustre de leon, J., Zabinsky, S. I., and Albers, R. C. (1991). J. Am. Chem. Soc. USA 113, 5135-5138.
16. Reponen, P., Sahlberg, C., Huhtala, P., Hurskainen, T., Thesleff, I., and Tryggvason, K. (1992). Molecular cloning of murine 72-kDa type IV collagenase and its expression during mouse development. J. Biol. Chem. 267, 7856-7862.
17. Stern, E. A., Newville, M., Ravel, B., Yacoby, Y., and Haskel, D. (1995). The UWXAFS analysis package: philosophy and details. Physica B 208/209, 117-122.
18. Van Wart, H., and Birkedal-Hansen, H. (1990). The Cysteine Switch: A Principle of Regulation of Metalloproteinase Activity with Potential Applicability to the Entire Matrix Metalloproteinase Gene Family. Proc. Natl. Acad. Sci. USA 87, 5578-5582.
19. Will, H., Atkinson, S. J., Butler, G. S., Smith, B., and Murphy G. (1996). The soluble catalytic domain of membrane type 1 matrix metalloproteinase cleaves the propeptide of progelatinase A and initiates autoproteolytic activation. J. Biol. Chem. 271, 17119-17123.
20. Zabinsky, S. I., Rehr, J. J., Ankudinov, A., Albers, R. C., and Eller, M. J. (1995). Multiple-scattering calculations of x-ray-absorption spectra. Phys. Rev. B 52, 2995-3009.

What is claimed is:

1. An antibody comprising an antigen recognition region capable of specifically binding a compound having the general Formula (I):

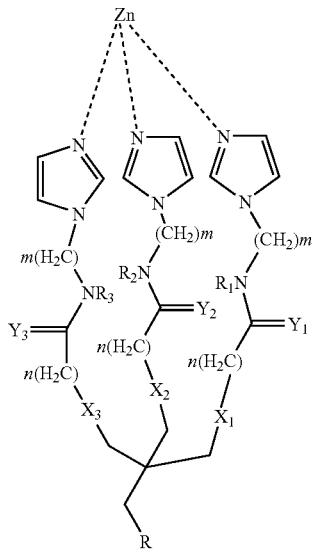

wherein:
m and n are each independently an integer from 1 to 6;
$X_1$-$X_3$ and $Y_1$-$Y_3$ are each O;
$R_1$-$R_3$ are each independently selected from the group consisting of hydrogen or alkyl; and
R is O—$(CH_2)_x$-C(=O)NR'—$(CH_2)_y$-NHR'
whereas:
x and y are each independently an integer from 1 to 6; and
R' is selected from the group consisting of hydrogen and alkyl;

the antibody being capable of inhibiting the activity of matrix metalloproteinase-9 (MMP-9) and matrix metalloproteinase-2 (MMP-2) with a Ki of less than 5 µM.

2. The antibody of claim 1, wherein said compound has the Formula (II):

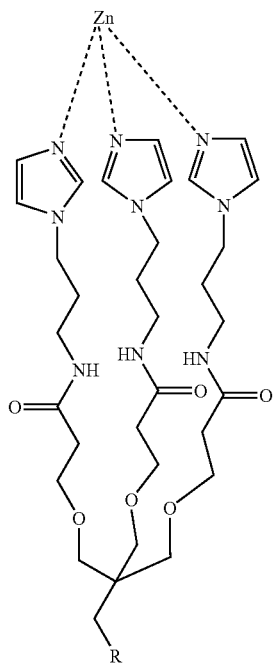

wherein R=O—$CH_2$—C(=O)NH—$CH_2$—$CH_2$—$NH_2$.

3. The antibody of claim 1, attached to a solid support.

* * * * *